United States Patent
Zhang et al.

(10) Patent No.: US 10,512,627 B2
(45) Date of Patent: Dec. 24, 2019

(54) ANTI-TUMOR COMPOUND AND THE MEDICAL USE THEREOF

(71) Applicant: Tianjin Medical University Cancer Institute and Hospital, Tianjin (CN)

(72) Inventors: Ning Zhang, Tianjin (CN); Yinsong Wang, Tianjin (CN); Ping Zhou, Tianjin (CN); Hua Guo, Tianjin (CN); Yi Luo, Tianjin (CN); Xishan Hao, Tianjin (CN); Hua Geng, Tianjin (CN)

(73) Assignee: Tianjin Medical University Cancer Institute and Hospital, Tianjin (CN)

( * ) Notice: Subject to any disclaimer, the term of this patent is extended or adjusted under 35 U.S.C. 154(b) by 20 days.

(21) Appl. No.: 15/508,516

(22) PCT Filed: Sep. 2, 2015

(86) PCT No.: PCT/CN2015/088842
§ 371 (c)(1),
(2) Date: Mar. 3, 2017

(87) PCT Pub. No.: WO2016/034126
PCT Pub. Date: Mar. 10, 2016

(65) Prior Publication Data
US 2017/0273933 A1 Sep. 28, 2017

(30) Foreign Application Priority Data
Sep. 3, 2014 (CN) .......................... 2014 1 0446415

(51) Int. Cl.
*A61K 31/337* (2006.01)
*A61K 31/192* (2006.01)
(Continued)

(52) U.S. Cl.
CPC .......... *A61K 31/337* (2013.01); *A61K 31/192* (2013.01); *A61K 45/06* (2013.01);
(Continued)

(58) Field of Classification Search
None
See application file for complete search history.

(56) References Cited

U.S. PATENT DOCUMENTS 7,700,615 B2 * 4/2010 Edwards ................ A61K 31/00
514/294

FOREIGN PATENT DOCUMENTS

| CN | 101627013 | 1/2010 |
| CN | 102807568 | 12/2012 |

(Continued)

OTHER PUBLICATIONS

Yasufuku et al., J. Infect. Chemother. (2010) 16:200-205.*
(Continued)

*Primary Examiner* — Alicia L Otton
(74) *Attorney, Agent, or Firm* — Hamre, Schumann, Mueller & Larson, P.C.

(57) ABSTRACT

The invention disclose a compound of formula (I), wherein, $R_1$ is selected from —H or C1-C6 hydrocarbon group, —$NH_2$, —OH, —O($CH_2$)$_n CH_3$ (n=0, 1 or 2), —N($CH_3$)$_2$, or —$CH_2$N($CH_3$)$_2$, $R_2$ is selected from an amino acid

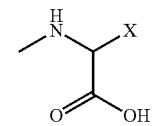

or an hydroxy acid

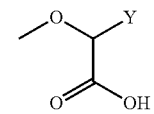

or —OH ($R_1$, $R_2$ are not —$CH_3$ and —OH at the same time), wherein X, Y are

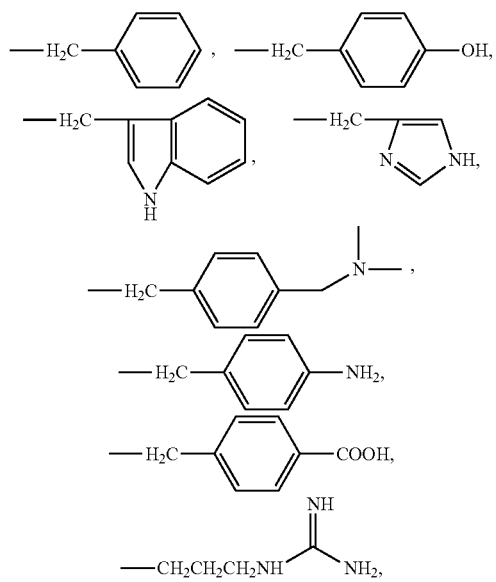

—H, —$CH_3$, —$CH_2OH$, —CH(OH)$CH_3$, —$CH_2SH$, —CH($CH_3$)$_2$, —$CH_2CH(CH_3)_2$, —CH($CH_3$)$CH_2CH_3$, —$CH_2CH_2SCH_3$, —$CH_2COOH$, —$CH_2CONH_2$, —$CH_2CH_2COOH$, —$CH_2CH_2CH_2CH_2NH_2$, or —$CH_2CH_2CONH_2$, $R_3$-$R_5$ are H or C1-C6 hydrocarbon group. The compound has a low toxicity, can significantly (Continued)

inhibit the migration and invasion of tumor cells in vitro, and can inhibit tumor metastasis in vivo in mice at low concentration, while showing notable sensitizing effect on cytotoxic anti-tumor drugs such as Paclitaxel etc.

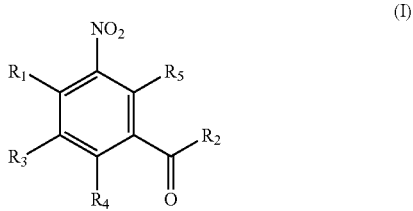

(I)

10 Claims, 16 Drawing Sheets

(51) Int. Cl.
  *A61K 45/06* (2006.01)
  *C07C 205/59* (2006.01)
  *C07C 229/60* (2006.01)
  *C07C 233/87* (2006.01)
  *C07C 231/00* (2006.01)

(52) U.S. Cl.
  CPC .......... *C07C 205/59* (2013.01); *C07C 229/60* (2013.01); *C07C 233/87* (2013.01); *A61K 2300/00* (2013.01); *C07C 231/00* (2013.01)

(56) References Cited

FOREIGN PATENT DOCUMENTS

| | | |
|---|---|---|
| CN | 104326937 | 2/2015 |
| JP | 2011026301 | 2/2011 |
| WO | 2007/141473 | 12/2007 |
| WO | 2011/099832 | 8/2011 |
| WO | 2014/086739 | 6/2014 |
| WO | WO 2015/127416 * | 8/2015 .......... A61K 31/715 |

OTHER PUBLICATIONS

Khalaf, Reema Abu et al., "Tryptophan and thiosemicarbazide derivatives: design, synthesis, and biological evaluation potential b-D-galactosidase and b-D-glucosidase inhibitors," Medical Chemistry Research. Dec. 9, 2014, vol. 23, No. 12. [Online], Retrieved from the internet: <https://www.researchgate.net/publication/269820597>, 25 pages. Cited in International Search Report.

Registry. "RN:1608722-99-1, 1608985-26-7, 1608984-34-4, 1608969-20-5, 1608893-96-4, 1608852-70-5, 1608840-67-0 et al." STN Columbus. American Chemical Society, 2015. May 26 and 27, 2014, 15 pages. Cited in International Search Report.

Xu, Bixue et al., "Synthesis and anti-tumor activity evaluation of Matijin-Su derivatives," Bioorganic Chemistry. Jun. 2, 2014, vol. 56, pp. 34-40. Cited in International Search Report.

Ronwin, Edward, "Optical Activity and the Direct Method of Acylation," Journal of Organic Chemistry. Oct. 31, 1957, vol. 22, pp. 1180-1183. Cited in International Search Report.

Ohano, Sadasuke et al., "Studies on Azoprotein Immunization. IV Synthesis of Haptenes (3). Nα-Aminobenzoyl-L-hisidines and Nw-Aminobenzoylhistamines." Yakugaku Zasshi. Dec. 31, 1957, vol. 77, No. 10, pp. 1105-1107. Cited in International Search Report.

Rieker, Anton et al., "Zur radikalishen Reaktionsweise von Isonitrilen" Justus Liebigs Annalen Der Chemie. Dec. 31, 1972, vol. 761, 13 pages. English abstract, cited in International Search Report.

Li, Menghui et al., "Basic Research of Cell Migration Inhibitor 4-methyl-3-nitro-benzoic Acid," Chinese Journal of Clinical Oncology. Dec. 31, 2010, vol. 37, No. 11, 8 pages. English abstract; cited in International Search Report.

International Search Report dated Nov. 25, 2015 for corresponding application No. PCT/CN2015/088842, 5 pages.

* cited by examiner

A: negative control; B: positive control; C: low dosage; D: medium dosage; E: high dosage

ANTI-TUMOR COMPOUND AND THE MEDICAL USE THEREOF

FIELD OF THE INVENTION

The invention belongs to the field of biochemical medicine, and more particularly to an anti-tumor compound and the medical use thereof, specifically relates to the inhibiting capability of compound on the migration and invasion of tumor cells, as well as the inhibiting effect on tumor metastasis in vivo in mice, so as to play a therapeutic role on tumors.

BACKGROUND OF THE INVENTION

Metastasis is one important characteristic of malignant tumor, and is also an important reason for causing low recovery rate of malignant tumor and high mortality in patients. Recently, researches have showed that metastasis of tumor cells is mainly induced by chemotaxis. Chemotaxis refers that a cell could sense the concentration gradient of chemicals in the outside environment, and move along the direction of concentration gradient. Scientists are dedicating to find a way to inhibit tumor metastasis by blocking the chemotaxis of tumor cells.

Hitherto, there is no specific drug to inhibit tumor metastasis on the international market, and there is no product classified as the subgroup of inhibiting tumor metastasis among the non-cytotoxic anti-tumor drugs.

SUMMARY OF THE INVENTION

To solve the problem of tumor metastasis, on the basis of (4'-methyl-3'-nitrobenzoylamino)-acetic acid compounds, a novel compound with good water-solubility and high tumor metastasis-inhibiting activity are synthesized and screened in the invention, which has been preliminarily proved for the possibility of being developed into the new drug for inhibiting tumor metastasis.

Our research group has found that, (4'-methyl-3'-nitrobenzoylamino)-acetic acid compound has strong inhibiting effect on the migration and invasion of various tumor cells, and has notable synergistic effect when combined with Paclitaxel, and that it is regarded as a good drug candidate.

Specifically, the invention relates to the following items:

1. A compound of formula I:

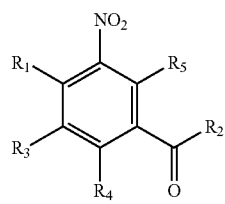

I wherein, $R_1$ is selected from the group consisting of —H or C1-C6 hydrocarbon group, —NH$_2$, —OH, —O(CH$_2$)$_n$CH$_3$ (n=0, 1 or 2), —N(CH$_3$)$_2$, —CH$_2$N(CH$_3$)$_2$, $R_2$ is selected from an α amino acid

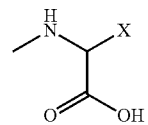

or an α hydroxy acid

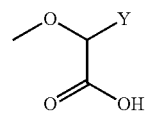

or —OH (provided that $R_1$, $R_2$ are not —CH$_3$ and —OH at the same time), wherein X, Y are

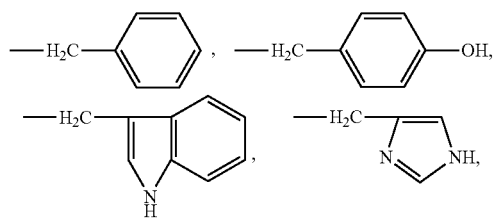

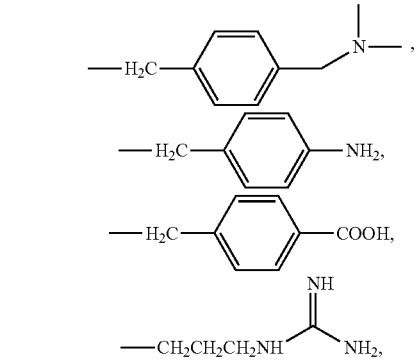

—H, —CH$_3$, —CH$_2$OH, —CH(OH)CH$_3$, —CH$_2$SH, —CH(CH$_3$)$_2$, —CH$_2$CH(CH$_3$)$_2$, —CH(CH$_3$)CH$_2$CH$_3$, —CH$_2$CH$_2$SCH$_3$, —CH$_2$COOH, —CH$_2$CONH$_2$, —CH$_2$CH$_2$COOH, —CH$_2$CH$_2$CH$_2$CH$_2$NH$_2$, or —CH$_2$CH$_2$CONH$_2$, $R_3$ to $R_5$ is H or C1-C6 hydrocarbon group.

2. The compound according to item 1, wherein, $R_1$ is H or C1-C6 hydrocarbon group, $R_2$ is α-amino acid, $R_3$ to $R_5$ are H.

3. The compound according to item 2, wherein, $R_2$ is L-phenylalanine, i.e. X is benzyl, $R_1$ is —CH$_3$, forming (S)2-(4'-methyl-3'-nitrobenzoylamino)-3-phenylpropionic acid.

4. A method for producing a compound according to any one of items 1-3, comprising the step of linking 2-$R_5$-4-$R_1$-5-$R_3$-6-$R_4$-3-nitrobenzoic acid and amino acid or hydroxy acid through amido bond, wherein $R_1$ is selected from the group consisting of —H or C1-C6 hydrocarbon group, —NH$_2$, —OH, —O(CH$_2$)$_n$CH$_3$ (n=0, 1 or 2), —N(CH$_3$)$_2$, —CH$_2$N(CH$_3$)$_2$, $R_3$ to $R_5$ are H or C1-C6 hydrocarbon group.

5. The producing method according to item 4, wherein, $R_1$ is —CH$_3$, $R_3$-$R_5$ are H, the amino acid is L-phenylalanine.

6. A pharmaceutical composition comprising a compound according to any one of items 1-3.

7. The use of the compound according to any one of items 1-3 for producing medicament for treating cancers.

8. The use of the compound according to any one of items 1-3 for producing medicament for inhibiting tumor metastasis.

9. The use of the compound according to any one of items 1-3 and another anti-tumor drug for producing medicament or kit for treating cancers, in which the another anti-tumor drugs is preferably a cytotoxic anti-tumor drug.

10. The use according to item 9, wherein the another anti-tumor drug is Paclitaxel.

The invention of compound, in particular (S)2-(4'-methyl-3'-nitrobenzoylamino)-3-phenylpropionic acid, has good water-solubility, and strong activity for inhibiting tumor metastasis, and is able to effectively inhibit the migration and invasion in vitro of various cell lines, such as MDA-MB-231, A549, etc., and is able to notably inhibit the metastasis of melanoma, breast cancer in situ, and lung cancer etc. models in mouse at lower concentration. Meanwhile, it has low toxicity and high safety, and shows significant sensitizing effect on the cytotoxic anti-tumor drug Paclitaxel, thus is a good candidate compound as an inhibitor for tumor metastasis, and is expected to fill the market vacancy of tumor metastasis inhibiting drugs.

DETAILED DESCRIPTION OF THE INVENTION

Further details will be described below for the technical solution of the invention. It should be noted that each of the embodiments could be combined in any manner as required.

On one aspect of the invention, it is provided a novel anti-tumor compound with the general formula as follow:

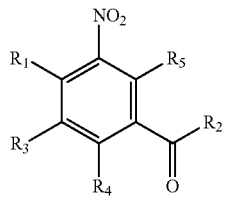

wherein, $R_1$ is selected from the group consisting of —H, C1-C6 hydrocarbon, —NH$_2$, —OH, —O(CH$_2$)$_n$CH$_3$ (n=0, 1 or 2), —N(CH$_3$)$_2$, —CH$_2$N(CH$_3$)$_2$, $R_2$ is selected from α amino acid

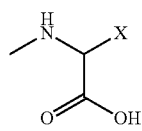

or α hydroxy acid

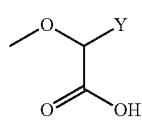

or —OH($R_1$, $R_2$ are not —CH$_3$ and —OH at the same time), wherein X, Y is

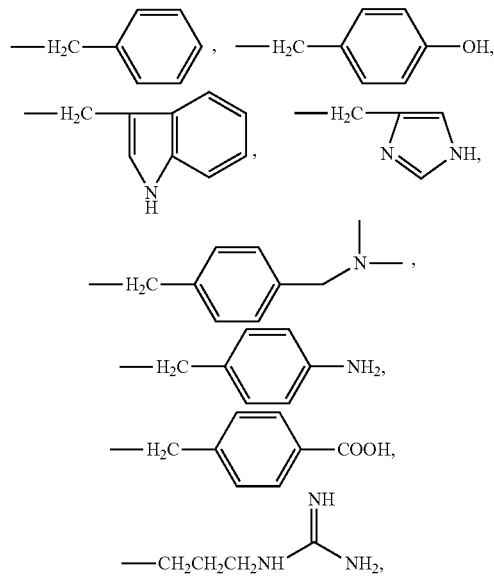

—H, —CH$_3$, —CH$_2$OH, —CHOHCH$_3$, —CH$_2$SH, —CH(CH$_3$)$_2$, —CH$_2$CH(CH$_3$)$_2$, —CH(CH$_3$)CH$_2$CH$_3$, —CH$_2$CH$_2$SCH$_3$, —CH$_2$COOH, —CH$_2$CONH$_2$, —CH$_2$CH$_2$COOH, —CH$_2$CH$_2$CH$_2$CH$_2$NH$_2$, or —CH$_2$CH$_2$CONH$_2$, and $R_3$-$R_5$ is H or C1-C6 hydrocarbon group.

In a preferred embodiment, $R_1$ is hydroxyl or amino, $R_2$ is hydroxy, $R_3$-$R_5$ is H, forming the compound 4-hydroxy-3-nitrobenzoic acid or 4-amino-3-nitrobenzoic acid.

In a further preferred embodiment, $R_1$ is methyl, $R_2$ is an amino acid, $R_3$-$R_5$ is H; and in a most preferred embodiment, $R_2$ is phenylalanine, that is, X is benzyl. In this case, the activity of the compound is strongest, and a compound with the name of (S)2-(4'-methyl-3'-nitrobenzoylamino)-3-phenylpropionic acid is formed, with the molecular formula of $C_{17}H_{16}N_2O_5$ and the molecular weight of 328.11.

The compound of the invention, in particular (S)2-(4'-methyl-3'-nitrobenzoylamino)-3-phenylpropionic acid, has good solubility, is water soluble, with solubility in water of 212±7 mg (25 □), and is highly soluble in dry ethanol, methanol, chloroform, dimethylformamide, dimethylsulfoxide etc.; and is able to significantly inhibit the migration and invasion of human breast cancer cell MDA-MB-231. Moreover, the compound has strong inhibiting activity on tumor metastasis, and tail vein administration of 0.5 mg/kg could significantly inhibit the metastasis of B16 mouse melanoma cell in C57BL/6 mouse in vivo.

On another aspect of the invention, it is provided a method for synthesis of the compound. In an embodiment, the synthetic method comprise the step of the attachment of 2-$R_5$-4-$R_1$-5-$R_3$-6-$R_4$-3-nitrobenzoic acid to an amino acid or hydroxy acid by amide bond, wherein $R_1$ is selected from the group consisting of —CH$_3$, —NH$_2$, —OH, —O(CH$_2$)$_n$CH$_3$ (n=0, 1 or 2), —N(CH$_3$)$_2$, —CH$_2$N(CH$_3$)$_2$, and $R_3$-$R_5$ are H or C1-C6 hydrocarbon group.

In a preferred embodiment, $R_1$ is preferably —CH$_3$, $R_3$-$R_5$ are H, and said amino acid is preferably phenylalanine. In the preferred embodiment, the procedure of the synthetic method comprises:

1) To appropriate amount of L-phenylalanine methyl ester, appropriate amount of tetrahydrofuran, dioxane, dimethylformamide, dimethylsulfoxide, anhydrous ethanol or methanol is added, and after dissolution, appropriate amount of sodium carbonate is added, with the mole ratio of L-phenylalanine methyl ester to sodium carbonate as 3:4, then catalytic amount of dimethylaminopyridine is added;

2) To 4-methyl-3-nitrobenzoic acid which is 0.5~10 folds relatively to L-phenylalaninemethyl ester in molar quantities, appropriate amount of dichlorosulfoxide is added, and after being heated under reflux at 90□ for 1~5 h, evaporated and dried with rotary evaporator, then small amount of tetrahydrofuran, dioxane, dimethylformamide, dimethylsulfoxide, anhydrous ethanol or methanol is added to dissolve the product. The dissolved product is added dropwise to the solution in step 1) with constant pressure dropping funnel. The reaction is heated at 40~100□ for 5~48 h, and the optimal condition of the reaction is heating at 60 □ for 16 h;

3) After the end of reaction, the sodium carbonate is removed by sucking filtration. The filtrate is concentrated with rotary evaporator, and then hydrolyzed with saturated lithium hydroxide solution. Concentrated hydrochloric acid is added until the occurrence of a large number of yellow precipitate, after sucking filtration and discard of filtrate, chloroform is added to the precipitate to dissolve, then (S)2-(4'-methyl-3'-nitrobenzoylamino)-3-phenylpropionic acid is separated using silica gel chromatography column.

In another embodiment of the invention, it is provided a method for purification of the compound, in particular (S)2-(4'-methyl-3'-nitrobenzoylamino)-3-phenylpropionic acid, which comprises:

1) The compound isolated by silica gel chromatography column, in particular (S)2-(4'-methyl-3'-nitrobenzoylamino)-3-phenylpropionic acid is dissolved in appropriate amount of solution of sodium carbonate in ultrapure water, pH=8~10, and after several times of sucking filtration to remove insoluble impurities, hydrochloric acid is added dropwise to the filtrate until the occurrence of a large amount of precipitate, and after sucking filtration, the precipitate is dried in vacuum to produce the product.

2) The second filtrate is added to 7~15 folds by volume of anhydrous ethanol, and after sucking filtration to remove the precipitate, the ethanol phase is concentrated with rotary evaporator, and added to 5~10 folds by volume of water adjusted to pH of 4~5 with hydrochloric acid, and after sucking filtration, the precipitate is dried in vacuum to produce the product.

On another aspect of the invention, it is provided a pharmaceutical composition, which comprises the above mentioned compound. Pharmaceutically acceptable adjuvant, excipient, disintegrating agent etc. may be comprised in the pharmaceutical composition. In an embodiment, it is provided a method for formulating (S)2-(4'-methyl-3'-nitrobenzoylamino)-3-phenylpropionic acid in experiments in vivo or in vitro:

1) Mother liquid of the cell experiments: 5 mg compound, in particular (S)2-(4'-methyl-3'-nitrobenzoylamino)-3-phenylpropionic acid is weighed accurately, and dissolved with 1 mL dimethyl sulfoxide. Then the mixture is added dropwise to 40 mL sterile phosphate-buffered solution (PBS) with stirring, and finally brought to 50 mL with volumetric flask. The final concentration of the drug is 100 µg/mL, with the content of dimethylsulfoxide as 2.0%;

2) Mother liquid I for the dosage form administrated by intravenous injection: Appropriate amount of the compound, in particular (S)2-(4'-methyl-3'-nitrobenzoylamino)-3-phenylpropionic acid is weighed accurately and mixed with 0.5~10 folds by mass of Pluronic F68, small amount of anhydrous ethanol is added and dissolved, and the mixture is added dropwise to sterile water or physiological saline, and 100 mg/mL sodium carbonate solution is added until the solution just become clear. Afterwards, water is added to bring to volume, 4<pH<9, with the content of ethanol as <2%, and the solution is sterilized through 0.22 µm film.

3) Mother liquid II for the dosage form administrated by intravenous injection: Appropriate amount of the compound, in particular (S)2-(4'-methyl-3'-nitrobenzoylamino)-3-phenylpropionic acid is weighed accurately and mixed with anhydrous sodium carbonate with molar ration of 1:1~3:1, preferably of 1.8:1. Sterile water or physiological saline is added and fully stirred and dissolved until the solution is clear, 4<pH<9, and the solution is sterilized through 0.22 µm film.

4) The dosage form for oral administration: Required amount of compound, in particular (S)2-(4'-methyl-3'-nitrobenzoylamino)-3-phenylpropionic acid is added to appropriate amount of solution of 1%~3% sodium carboxymethylcellulose, and the mixture is homogenized for 5~10 min with a homogenizer at 30,000 rpm.

On another aspect of the invention, it is provided a use of the compound and the pharmaceutical composition comprising the compound for producing medicine. In one embodiment, the compound and the pharmaceutical composition comprising the compound is used for producing medicines for treating cancer; In a preferred embodiment, the cancer includes lung cancer, breast cancer, melanoma etc.; In a more preferred embodiment, the compound and the pharmaceutical composition comprising the compound is used for treating cancer by inhibiting the migration of the tumor cells.

In a specific embodiment, the method for studying the effects of the compound, in particular (S)2-(4'-methyl-3'-nitrobenzoylamino)-3-phenylpropionic acid, on the inhibition of tumor metastasis comprises the following steps:

1) The pharmacodynamic activity of the ability of (S)2-(4'-methyl-3'-nitrobenzoylamino)-3-phenylpropionic acid for inhibiting the migration of tumor cells is verified by cell scratch assay;

2) The pharmacodynamic activity of the ability of (S)2-(4'-methyl-3'-nitrobenzoylamino)-3-phenylpropionic acid for inhibiting the invasion of tumor cells is verified by Transwell invasion assay;

3) An metastasis model of B16 mouse melanoma is constructed by direct injection of B16 cells into tail vein in C57BL/6 mouse, and the ability of a drug for inhibiting tumor metastasis is determined by counting the number of the metastatic tumors on lung. Such a model mimics the metastatic process of cancer cells from the circulatory system to the target organ, which is more similar with the metastatic way of tumor cells in the bodies of patients with advanced cancer.

4) An in situ breast cancer model is constructed by in situ inoculating nude mice with 4T1 cells which are stably transfected with Luciferase, and the number of metastatic tumors on the lung is detected by in vivo imaging system. Such a model mimics the occurrence and metastasis of breast cancer.

5) A lung cancer model of mouse is established by subcutaneous inoculation of Lewis lung cancer cells in C57BL/6 mouse, because of the characteristic of Lewis lung cancer cell of specific metastasis toward the lung, and the ability of a drug for inhibiting the metastasis of the tumor cells may be determined by counting the number of the metastatic tumors on lung.

On another aspect of the invention, it is provided the use of the compound, in particular (S)2-(4'-methyl-3'-nitrobenzoylamino)-3-phenylpropionic acid and other anti-tumor drugs for producing drugs or kits for treating cancers.

In an embodiment, said other anti-tumor drug is a cytotoxic anti-tumor drug.

In a specific example, the invention provides the use of the compound, in particular (S)2-(4'-methyl-3'-nitrobenzoylamino)-3-phenylpropionic acid and Paclitaxel for producing drugs or kits for treating cancers. In a specific embodiment, the synergistic effect of the compound on the inhibition of the proliferation of MDA-MB-231 cells by Paclitaxel is evaluated by MTT assay.

EXAMPLES

Figure 1:
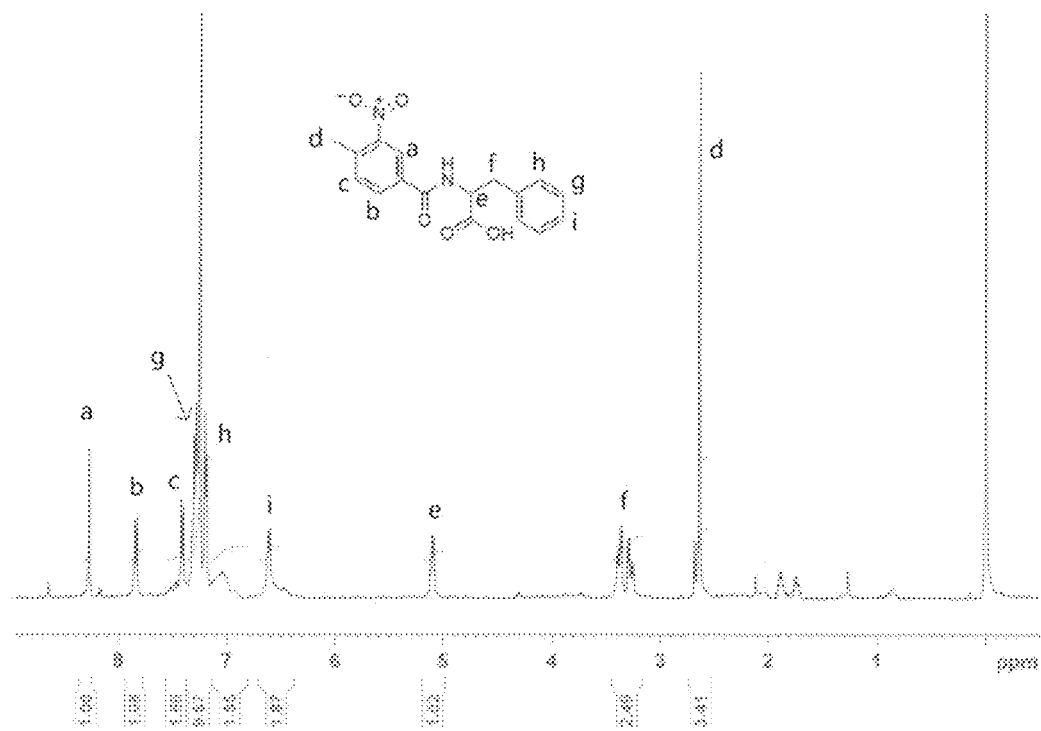
FIG. 1. The NMR spectrum of the product in Example 1, (S)2-(4'-methyl-3'-nitrobenzoylamino)-3-phenylpropionic acid.

The source of main reagents and materials:

MDA-MB-231, A549 cell lines are purchased from American Type Culture Collection (Manassas, Va., USA); B16 cell is purchased from Basic Medical Cell Center, Institute of Basic Medical Sciences, Chinese Academy of Medical Sciences; LLC cell line is purchased from the cell library of China Center for Type Culture Collection; DMEM/HIGH GLUCOSE (1×) culture medium and fetal bovine serum are purchased from Thermo Scientific (the product numbers are SH30022.01B and SV30087.02 respectively); Transwell chamber is purchased from MILLIPORE (product number: PIEP12R48), Matrigel is purchased from BD company, USA; both 24-well plate and 60 mm culture dish are purchased from Corning; Paclitaxel is purchased from Dalian MeiLun Biological Technology Co. Ltd; MTT is purchased from SIGMA; the reagents for chromatography and the chromatography column are purchased from DIKMA; poloxamer 188 and polyoxyethylene 35 castor oil are purchased from BASF SE, Germany; sodium carboxymethylcellulose is purchased from Tianjin KeMiOu Chemical Reagent Company; the reagents related to the synthesis are purchased from Beijing J&K Scientific Co. Ltd; C57BL/6 mouse, nude mice and KM mice are purchased from Beijing Rital River experimental animal technology Co. Ltd (License Number: SCXK (Jing) 2012-0001); mouse in vivo imaging system, IVIS Spectrum FMT1000, PerkinElmer.

The invention will be described in detail by Examples below, which Examples are merely used to further illustrate the invention, and cannot be construed as the limitation for the scope of the invention, and some non-essential modifications and adjustments made for the content by those skilled in the art according to the above contents of the invention, fall into the scope of the invention.

Example 1

The synthesis and structural characterization of (S)2-(4'-methyl-3'-nitrobenzoyl amino)-3-phenylpropionic acid.

Figure 2:
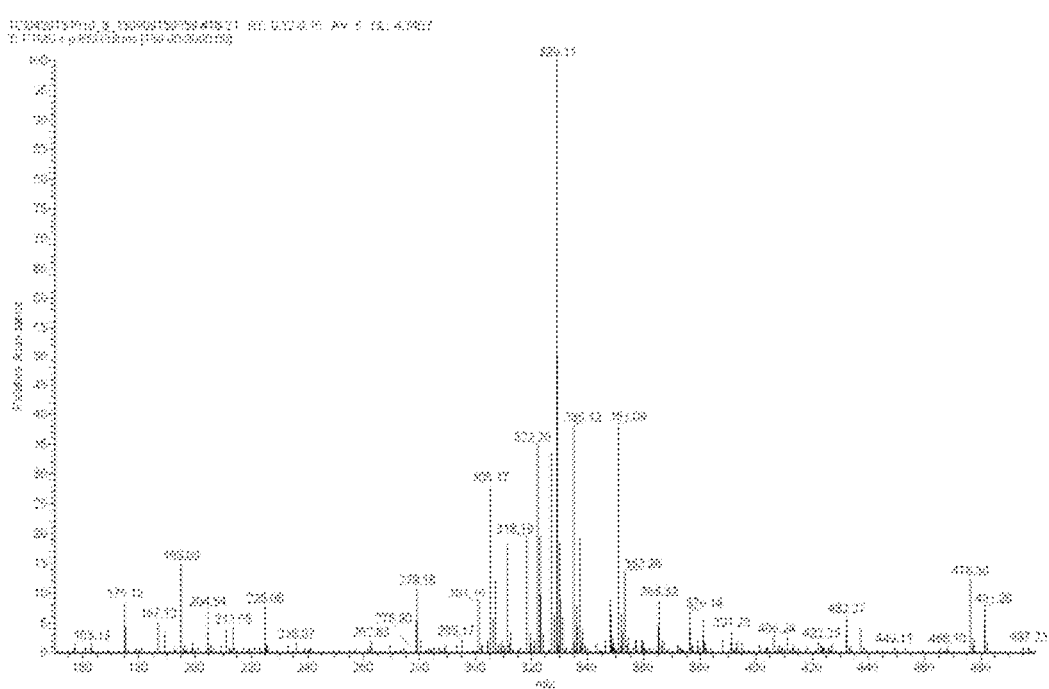
FIG. 2. The mass spectrum of the product in Example 1, (S)2-(4'-methyl-3'-nitrobenzoylamino)-3-phenylpropionic acid.

1) 64 g L-phenylalaninemethyl ester was weighed, then 400 mL tetrahydrofuran was added and heated at 50□ to dissolve, and after dissolution 42 g sodium carbonate was added, followed by stirring for 15 min, and 2 g dimethylaminopyridine was added;

2) 163 g 4-methyl-3-nitrobenzoic acid was weighed, then 450 mL dichlorosulfoxide was added, and heated at 90 □ under reflux for 3 h. After evaporating and drying with a rotary evaporator, 200 mL tetrahydrofuran was added to dissolve the product. Then the dissolved product was added dropwise to the solution described in 1) with constant pressure dropping funnel, and heated at 60 □ for 16 h;

3) After the end of reaction, the precipitate was removed by sucking filtration. The filtrate was concentrated to about 300 mL with a rotary evaporator, and then added to 2.4 L saturated lithium hydroxide solution, and stirred at room temperature for 3 h. Concentrated hydrochloric acid was added dropwise until the occurrence of a large amount of yellow precipitate, and the filtrate was discarded after sucking filtration. 1 L chloroform was added to dissolve the precipitate, and after concentration with a rotary evaporator, the precipitate was separated out after standing, and the precipitate was discarded after sucking filtration;

4) The concentrate was separated using silica gel chromatography column. Ethyl acetate:petroleum ether=1:2, with 1.4% glacial acetic acid was used first to flow through the column to elute 4-methyl-3-nitrobenzoic acid, and then methanol:dichloromethane=1:1, with 1.4% glacial acetic acid was used to flow through the column to elute (S)2-(4'-methyl-3'-nitrobenzoylamino)-3-phenylpropionic acid;

5) The mobile phases containing (S)2-(4'-methyl-3'-nitrobenzoylamino)-3-phenylpropionic acid were combined, and rotated with a rotary evaporator to be substantially dry, then put in to vacuum drying oven and dried at 45□ for 72 h;

6) The structure of the product was verified by $^1$H-NMR and mass spectra, with yield of 75.83%. NMR spectrum was shown in FIG. 1, and the mass spectrum was shown in FIG. 2.

Example 2

The purification of (S)2-(4'-methyl-3'-nitrobenzoylamino)-3-phenylpropionic acid and the detection of the purity.

1) (S)2-(4'-methyl-3'-nitrobenzoylamino)-3-phenylpropionic acid isolated by silica gel chromatography column was dissolved in appropriate amount of solution of sodium carbonate in ultrapure water, pH=8~10, and after sucking filtration to remove insoluble impurities, hydrochloric acid was added dropwise to the filtrate until the occurrence of a large amount of precipitate, and after sucking filtration, precipitate was dried in vacuum to produce the product. The second filtrate was added to 7~15 folds by volume of anhydrous ethanol, and the precipitate was removed by sucking filtration, then the ethanol phase was concentrated with rotary evaporator, then added to 5~10 folds by volume of water adjusted to pH of 4~5 by hydrochloric acid, and after sucking filtration, the precipitate was dried in vacuum, that was the product remained in aqueous phase.

Figure 3:
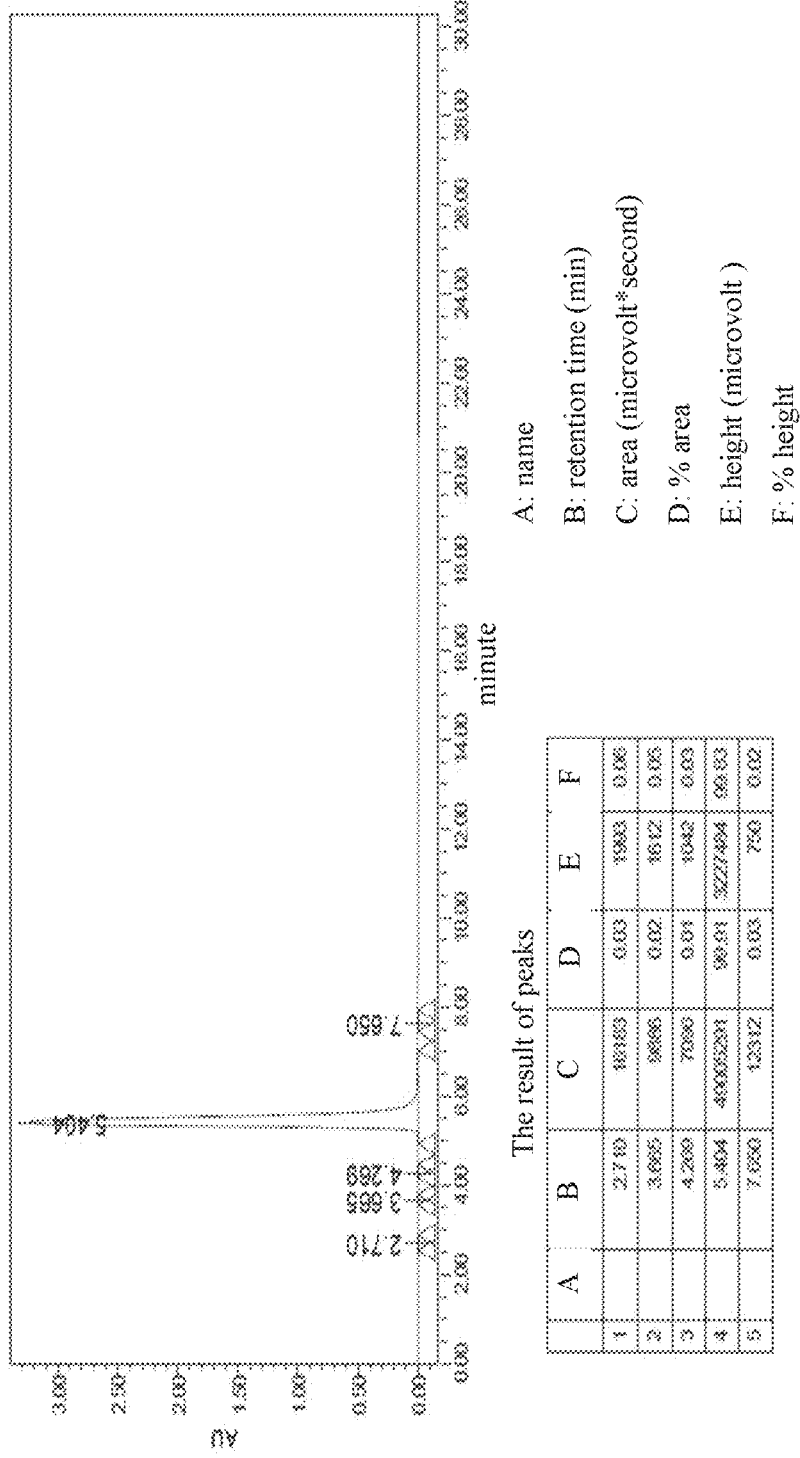
FIG. 3. The detection of the purity of (S)2-(4'-methyl-3'-nitrobenzoylamino)-3-phenylpropionic acid in Example 2.
Figure 4:
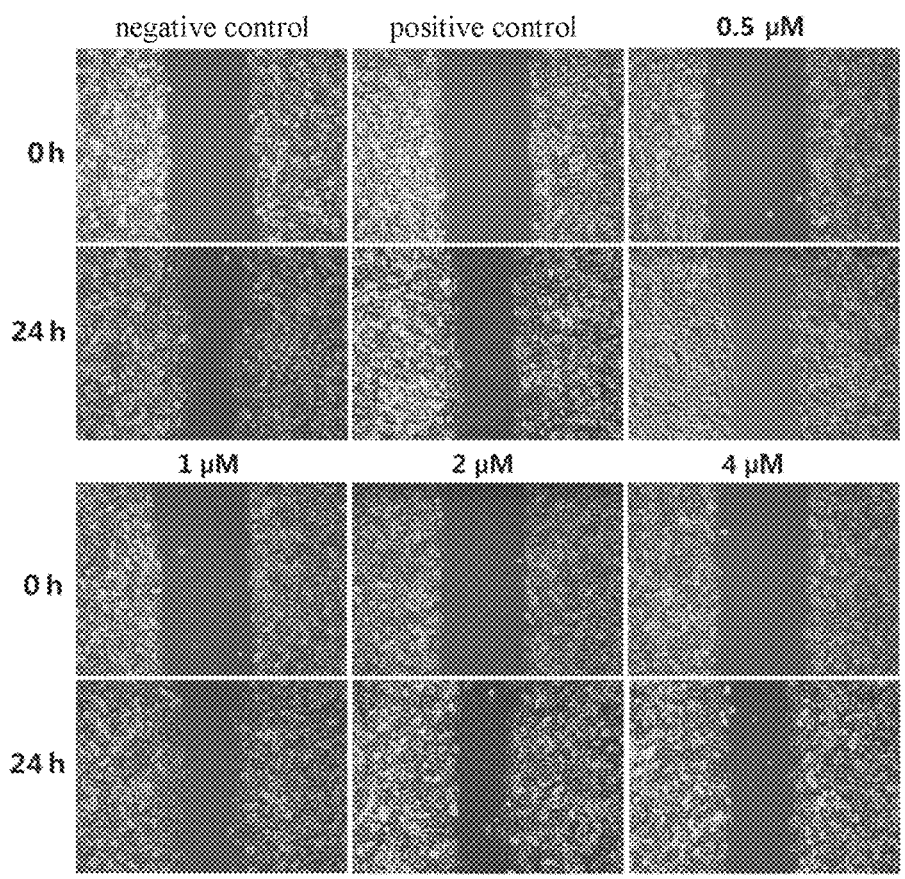
FIG. 4. The inhibition of (S)2-(4'-methyl-3'-nitrobenzoylamino)-3-phenylpropionic acid for the migration ability of MDA-MB-231 cells in Example 3.
Figure 5:
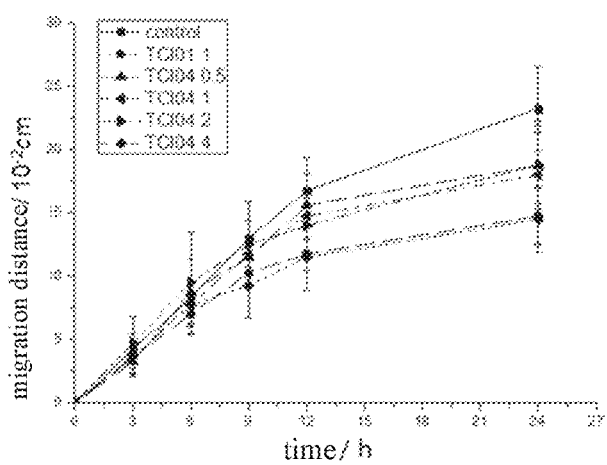
FIG. 5. The statistics of the inhibition of (S)2-(4'-methyl-3'-nitrobenzoylamino)-3-phenylpropionic acid for the migration ability of MDA-MB-231 cells in Example 3.

2) The purified (S)2-(4'-methyl-3'-nitrobenzoylamino)-3-phenylpropionic acid was weighed accurately, and formulated into 1 mg/mL of standard solution with mobile phase. The analysis was performed according to the following condition for chromatography: chromatography column: Vercopak C18(403091), 4.6 mm×250 mm, particle size of 5 μm, ODS-2; column temperature: 30□; mobile phase: acetonitrile:pH2.5 phosphate buffer (containing 0.2% triethylamine, 10 mmol sodium dihydrogen phosphate)=45:55 (v/v); flow rate: 1 mL/min; Detected wavelength: λ=230 nm. Detection result: the retention time of (S)2-(4'-methyl-3'-nitrobenzoylamino)-3-phenylpropionic acid was 5.404 min;

After integral analysis with the software in the instrument, the purity was 99.91%. The results of the experiments were shown in FIG. 3.

Example 3

The inhibiting ability of (S)2-(4'-methyl-3'-nitrobenzoylamino)-3-phenylpropionic acid for the migration of human breast cancer cell MDA-MB-231 was tested by scratch assay.

The MDA-MB-231 cells in logarithmic growth phase were plated in the 6-well plate with the density of $1\times10^6$/3 mL, and the drug was added after 12 h, with 100 μL per well. The final concentrations of (S)2-(4'-methyl-3'-nitrobenzoylamino)-3-phenylpropionic acid (TCI04) were 0.5, 1, 2, and 4 μmol/L, respectively. The negative control was 100 μL sterilized water with 2% DMSO and the positive control was 1 μmol/L 4-methyl-3-nitrobenzoic acid (TCI01). After 12 h, the culture medium was removed, and the plate was washed 3 times with PBS, and 3 ml culture medium without fetal bovine serum and 100 μL drug (concentration was the same as above) per well were added. 12 h later, 10 μL tips were used to scratch, and after washing 4 times with PBS, 3 ml culture medium without fetal bovine serum per well was added. The distance of cell migration was recorded every 3 h under the inverted microscope, and the photos were taken at 0 h and 24 h. The result was as follows: the coalescence speed of cell scratch in experimental group was significantly slower than the negative control, indicating that (S)2-(4'-methyl-3'-nitrobenzoylamino)-3-phenylpropionic acid significantly inhibited the migration ability of MDA-MB-231 cell.

Example 4

The inhibiting ability of (S)2-(4'-methyl-3'-nitrobenzoylamino)-3-phenylpropionic acid for the migration of human lung adenocarcinoma cell A549 was tested by scratch test.

Figure 6:
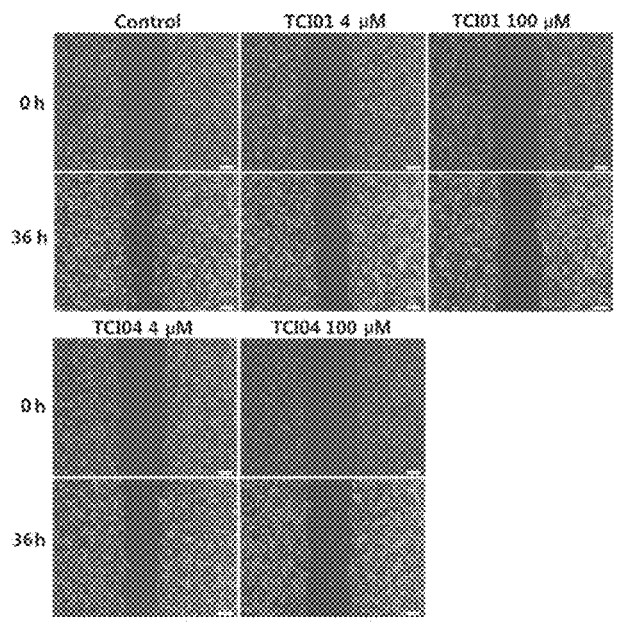
FIG. 6. The inhibition of (S)2-(4'-methyl-3'-nitrobenzoylamino)-3-phenylpropionic acid for the migration ability of A549 cells in Example 4.
Figure 7:
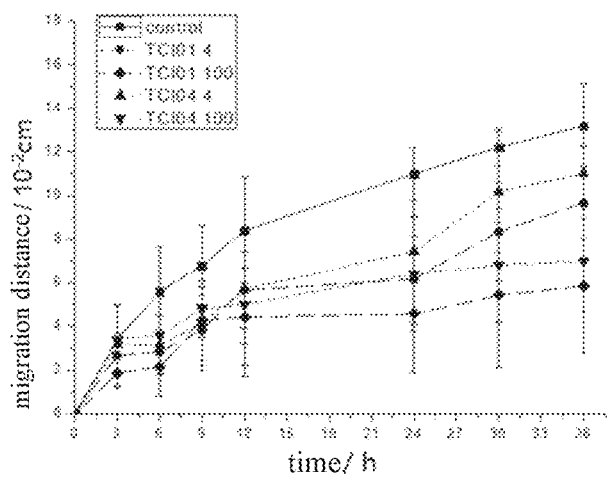
FIG. 7. The statistics of the inhibition of (S)2-(4'-methyl-3'-nitrobenzoylamino)-3-phenylpropionic acid for the migration ability of A549 cells in Example 4.

A549 cells in logarithmic growth phase were plated in the 6-well plate with the density of $5\times10^5$/3 mL, and after 12 h, the drug was added, with 100 μL per well. The final concentrations of (S)2-(4'-methyl-3'-nitrobenzoylamino)-3-phenylpropionic acid (TCI04) were 4 and 100 μmol/L respectively. The negative control was 100 μL sterilized water with 2% DMSO and the positive control was 4, 100 μmol/L 4-methyl-3-nitrobenzoic acid (TCI01). After 36 h, the medium was removed, and after washing 3 times with PBS, 3 ml culture medium without fetal bovine serum and 100 μL drug (concentration was as above) per well were added. 6 h later, 200 μL tips were used to scratch, and after washing 4 times with PBS, 3 ml medium without fetal bovine serum per well was added. The distance of cell migration was recorded every 3 h under the inverted microscope, and photos were taken at 0 h and 36 h. The result was as follows: the coalescence speed of cell scratch in experimental group was significantly slower than the negative control, indicating that (S)2-(4'-methyl-3'-nitrobenzoylamino)-3-phenylpropionic acid significantly inhibited the migration ability of A549 cells. Experimental results were shown in FIG. 6 and FIG. 7.

Example 5

The inhibiting ability of (S)2-(4'-methyl-3'-nitrobenzoylamino)-3-phenylpropionic acid for the invasion of human breast cancer cell MDA-MB-231 was tested by Transwell invasion assay.

Figure 8:
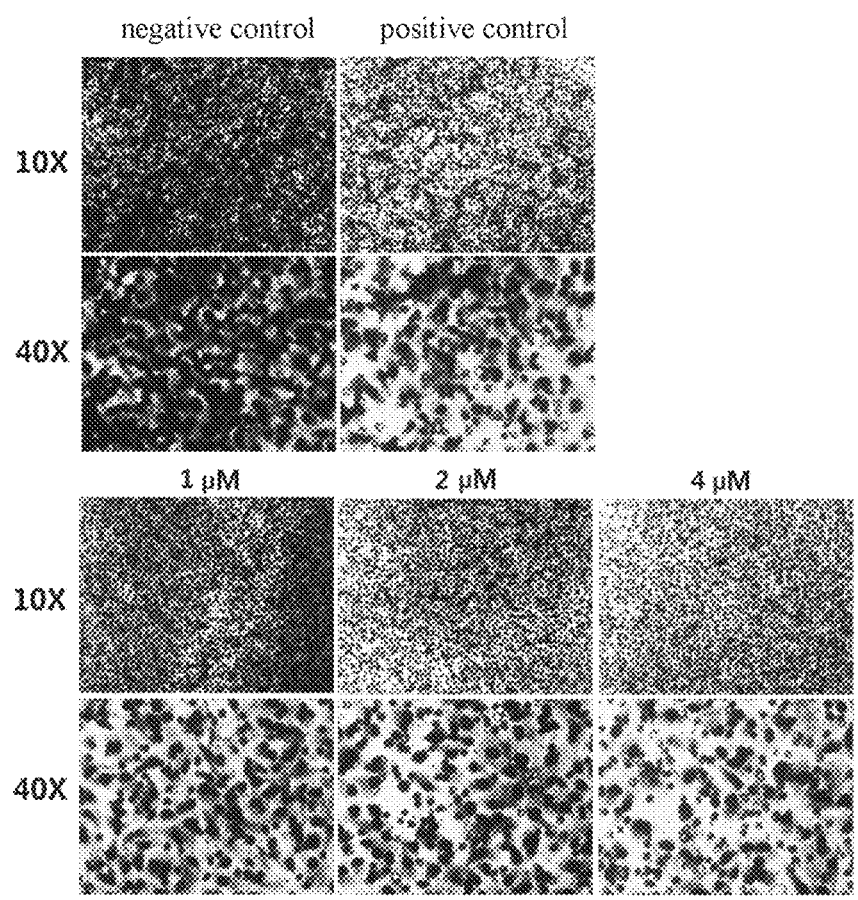
FIG. 8. The inhibition of (S)2-(4'-methyl-3'-nitrobenzoylamino)-3-phenylpropionic acid for the invasion ability of MDA-MB-231 cells in Example 5.
Figure 9:
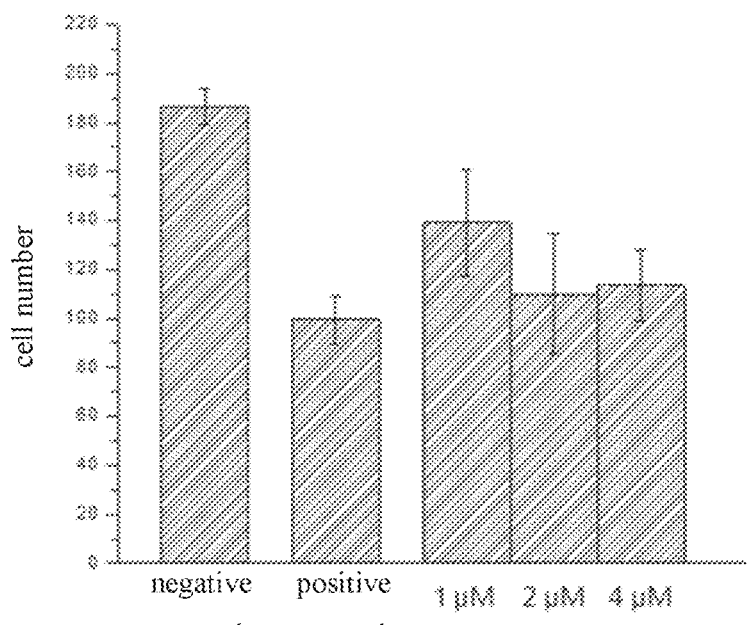
FIG. 9. The statistics of the inhibition of (S)2-(4'-methyl-3'-nitrobenzoylamino)-3-phenylpropionic acid for the invasion ability of MDA-MB-231 cells in Example 5.

1) Gel placement into the Transwell chamber: Matrigel was melted under ice-bath of 4° C. overnight, and diluted with pre-cooled serum free DMEM medium at a ratio of 1:3. Transwell chamber was put in the 24-well plate, and 50 μL gel solution was added per chamber, stayed at 37° C. for 1 h, then 200 μL serum free DMEM medium was added and stayed for 15 min to make the gel reconstitute, and finally the medium was removed for stand-by;

2) MDA-MB-231 cells in logarithmic growth phase were plated in 6-well plate with the density of $1 \times 10^6/3$ mL, and after 12 h, the drug was added, with 100 μL per well. The final concentrations of (S)2-(4'-methyl-3'-nitrobenzoylamino)-3-phenylpropionic acid were 1, 2, and 4 μmol/L, respectively. The negative control was 100 μL sterilized water with 2% DMSO and the positive control was 1 μmol/L 4-methyl-3-nitrobenzoic acid. After 12 h, the medium was removed, followed by washing 3 times with PBS, and 3 ml medium without fetal bovine serum and 100 μL drug (concentration is as above) per well were added. 12 h later, each group of cells was digested with 0.05% typsine, and resuspended in DMEM without fetal bovine serum. The cell number was counted and the cells were seeded at the density of $2 \times 10^5/200$ μL into the Transwell chamber with the Matrigel. The 600 μL DMEM with 20% fetal bovine serum was added at the bottom of the chamber;

3) 24 h later, the chambers were taken out, and the cells were stained by 3-step staining method, and photos were taken under the inverted microscope, at 400×, and for each chamber, uniform visual fields with 5 cells were chosen for counting;

4) The experimental results were shown in FIGS. 8 and 9. The cell number in experimental group was significantly less than the negative control. According to the statistics analysis, as compared to the negative control, for the 3 concentrations in the experimental group $P<0.01$, with very significant difference; as compared to the positive control, the experimental group 1 μmol/L has significant difference ($P<0.05$), and experimental groups 2, 4 μmol/L has no significant difference ($P>0.05$). The result indicates the ability of (S)2-(4'-methyl-3'-nitrobenzoylamino)-3-phenylpropionic acid to inhibit the invasion ability of MDA-MB-231 cells through Matrigel.

Example 6

The ability of (S)2-(4'-methyl-3'-nitrobenzoylamino)-3-phenylpropionic acid for inhibiting tumor metastasis in vivo was tested by artificial metastasis model of B16 mice melanoma.

Figure 10:
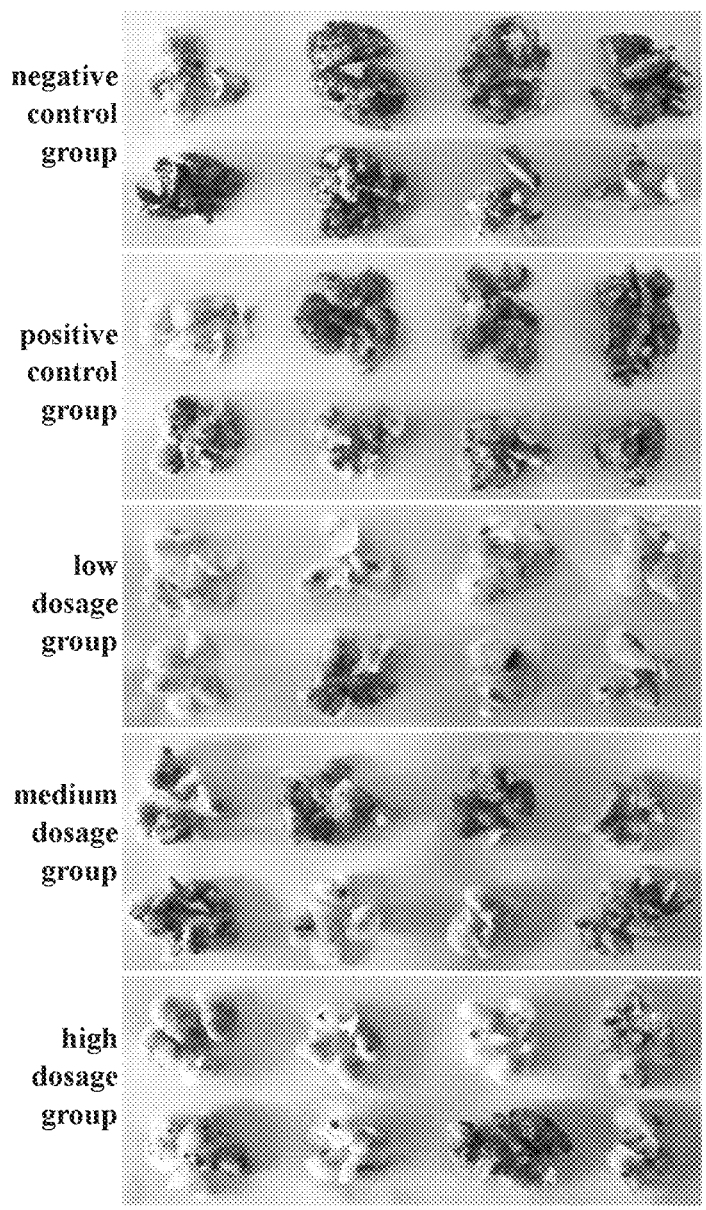
FIG. 10. The inhibition of (S)2-(4'-methyl-3'-nitrobenzoylamino)-3-phenylpropionic acid for the metastasis of B16 melanoma cells in vivo in C57BL/6 mouse in Example 6.
Figure 11:
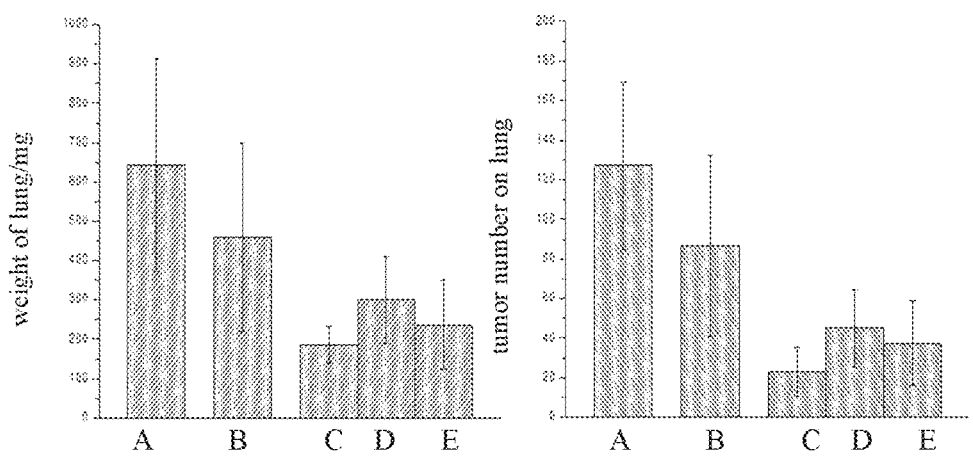
FIG. 11. The statistics of the inhibition of (S)2-(4'-methyl-3'-nitrobenzoylamino)-3-phenylpropionic acid for the metastasis of B16 melanoma cells in vivo in C57BL/6 mouse in Example 6.

1) Mice grouping: C57BL/6 of SPF grade, 5 weeks old, 18~22 g, 8 mice for each group, half male and half female;

2) The mother liquid of (S)2-(4'-methyl-3'-nitrobenzoylamino)-3-phenylpropionic acid for the dosage form administrated by intravenous injection was diluted to 0.8 mg/mL, 0.2 mg/mL, 0.05 mg/mL by adding sterilized water. The dosage for administration in mice was as follows: high dosage group of 8 mg/kg; medium dosage of 2 mg/kg; low dosage group of 0.5 mg/kg. Negative control was 0.8 mg/mL aq. Pluronic F68 solution with 0.25% ethanol; The positive control was 3.2 mg/mL aq. 4-methyl-3-nitrobenzoic acid solution, with dosage of 32 mg/kg;

3) B16 cells in logarithmic growth phase were digested with 0.05% typsine for 1 min, and after centrifugation at 1000 rpm for 5 min, the supernatant was discarded and the cells were resuspended and counted. After washing 3 times with physiological saline, the cells were resuspend and adjusted to the concentration of $2.5 \times 10^5$/mL with physiological saline. 0.2 ml cell suspension was injected via tail vein for each mouse;

4) Drug Administration was started immediately after the injection of the cell suspension, the administration routine was intravenous injection via tail vein, twice a day for 21 days continuously;

5) After the completion of the experiment, the mice were sacrificed and the lungs were taken, the number and size of melanomas on the lungs was counted, and the weight of the lungs were weighed;

6) The experimental results were shown in FIGS. 10 and 11, and for the negative control, the lungs of most of the mice were necrotic via metastasis with abnormal shape. For the experimental group, fewer tumors can be seen on the lungs with small size, and the lungs had normal shapes. After statistic analysis of the tumor numbers on the lungs and lung weights, as compared with the negative control, all the 3 concentrations in the experimental group had very significant difference ($P<0.01$); as compared with the positive control, all the 3 concentrations in the experimental group had significant difference ($P<0.05$) (for the individuals with metastatic necrosis of entire lung, since the number of tumors was too many to count, and the number was far more than 150, and a minimum value of 150 was take into the statistic analysis), indicating that (S)2-(4'-methyl-3'-nitrobenzoylamino)-3-phenylpropionic acid effectively inhibited the metastasis of B16 cells in mice in vivo.

Example 7

The ability of (S)2-(4'-methyl-3'-nitrobenzoylamino)-3-phenylpropionic acid for inhibiting tumor metastasis in vivo was tested by in situ model of breast cancer in nude mouse.

1) Mice grouping: Nude female mice of SPF grade, 5 weeks old, 18~22 g, 8 mice for each group;

2) The mother liquid of (S)2-(4'-methyl-3'-nitrobenzoylamino)-3-phenylpropionic acid (TCI04) for the dosage form administrated by intravenous injection was diluted to 2 mg/mL, 0.1 mg/mL by adding sterilized water. The dosage for administration in mice was as follows, high dosage of 20 mg/kg; low dosage of 1 mg/kg. The negative control was 2 mg/mL aq. Pluronic F68 solution with 0.25% ethanol; The positive control was 5 mg/mL aq. 4-methyl-3-nitrobenzoic acid (TCI01) water solution with administration dosage of 50 mg/kg;

3) 4T1-luciferase cells in logarithmic growth phase were digested with 0.05% typsine for 1 min, after centrifugation at 1000 rpm for 5 min, the supernatant was discarded and the cells were resuspended and counted. After washing 3 times with physiological saline, the cells were resuspended and adjust to the concentration of $5 \times 10^6$/mL with physiological saline. 0.1 ml cell suspension was inoculated into the second pair of breast on the right for each mouse;

4) One week after the inoculation, administration was started, and the administration routine was intravenous injection via tail vein, twice a day for 21 days continuously;

5) After the completion of the administration, the mice were detected by in vivo imaging system for the condition of tumor metastasis and immediately sacrificed; the lungs alone were detected by the in vivo imaging system for the light intensity to determine the number of tumor metastasis.

Figure 12:
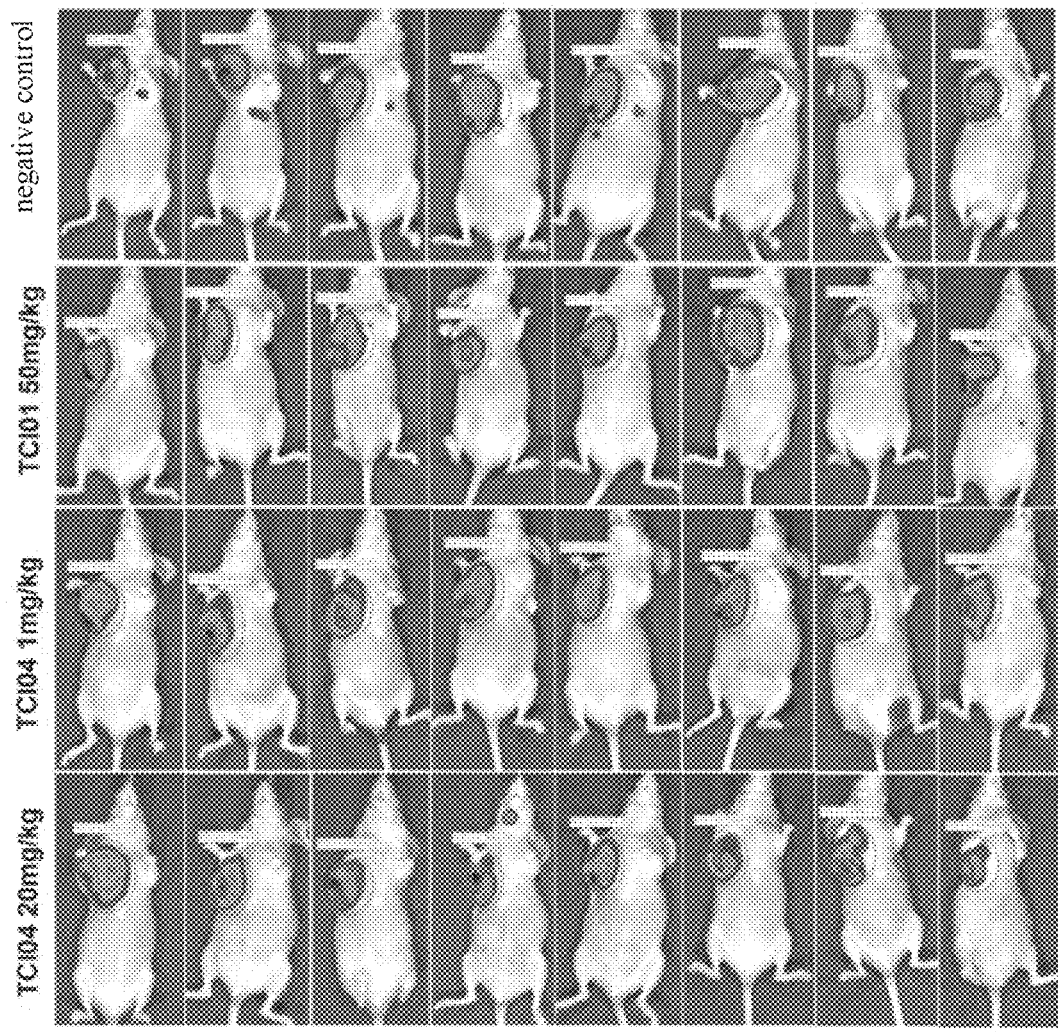
FIG. 12. The entire metastasis of tumor in mice in Example 7.
Figure 13:
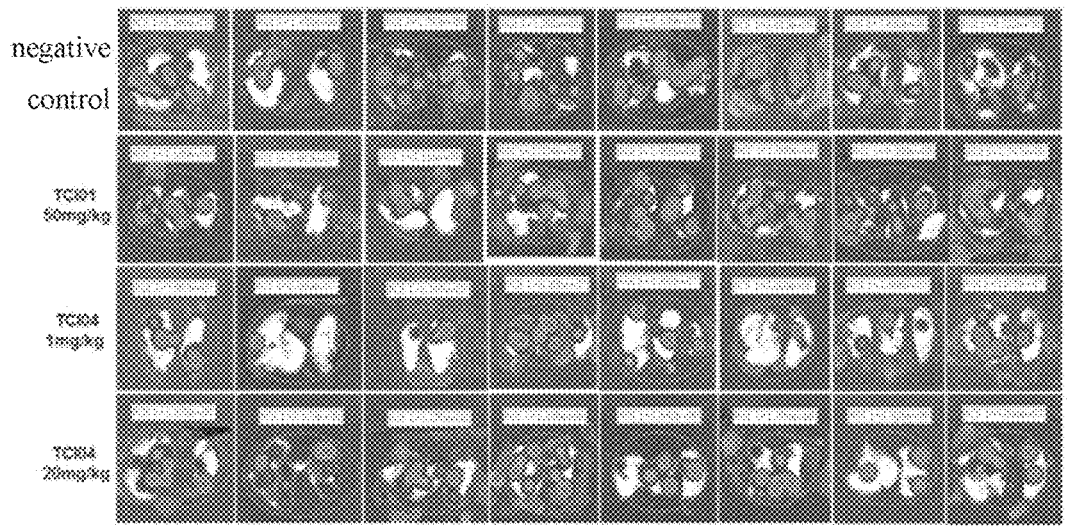
FIG. 13. The lung metastasis of tumor in mice in Example 7.
Figure 14:
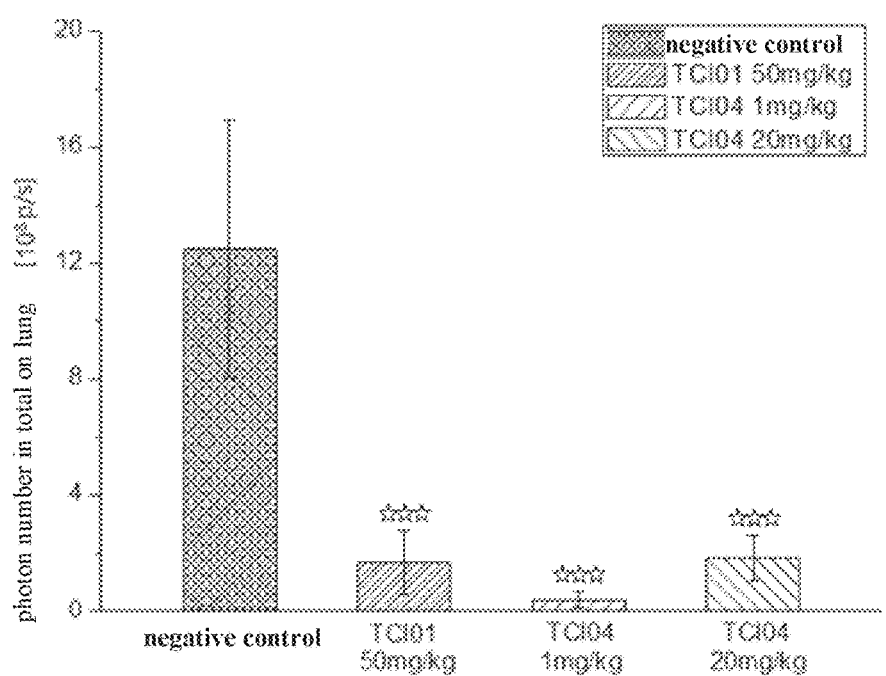
FIG. 14. The statistics of the lung metastasis of tumor in mice in Example 7.

6) The experimental results were shown in FIGS. 12, 13 and 14, and for the experimental group and TCI01 group, the light intensity of the whole lung was significantly weaker than the negative control, with very significant difference ($P<0.01$) shown in statistics results; as compared with TCI01 group, the experimental group also had significant difference (P<0.05), which indicates that (S)2-(4'-methyl-3'-nitrobenzoylamino)-3-phenylpropionic acid effectively inhibited the metastasis of 4T1 cells in mice in vivo.

Example 8

The ability of (S)2-(4'-methyl-3'-nitrobenzoylamino)-3-phenylpropionic acid for inhibiting tumor metastasis in vivo was tested by Lewis lung cancer metastasis model in mice.

Figure 15:
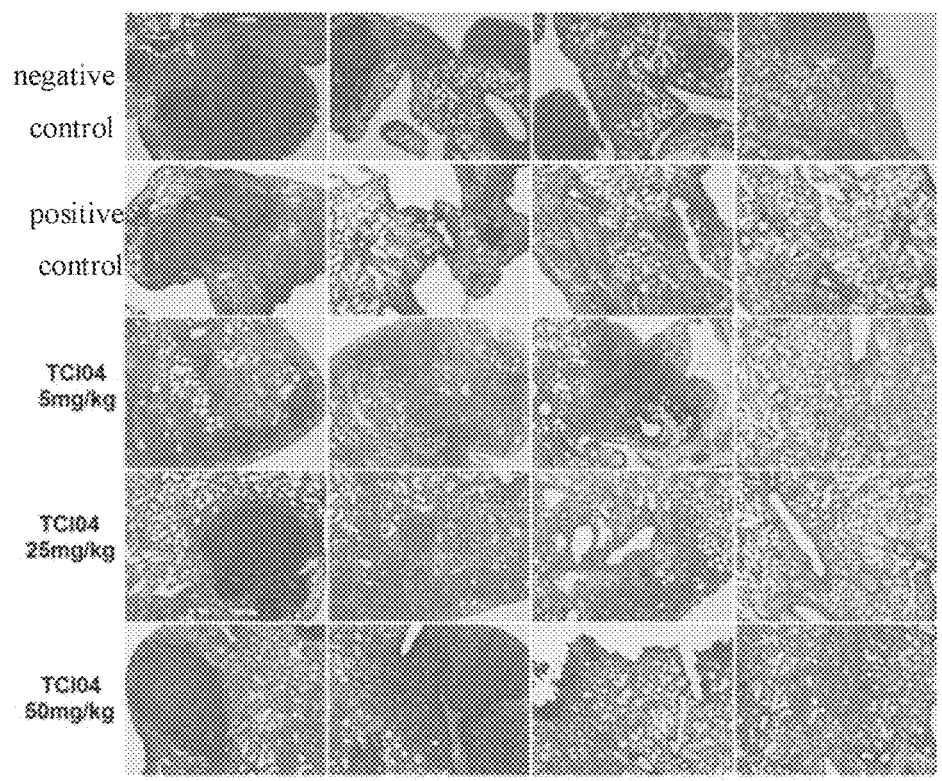
FIG. 15. HE staining of the histological section of lung in mice in Example 8.
Figure 16:
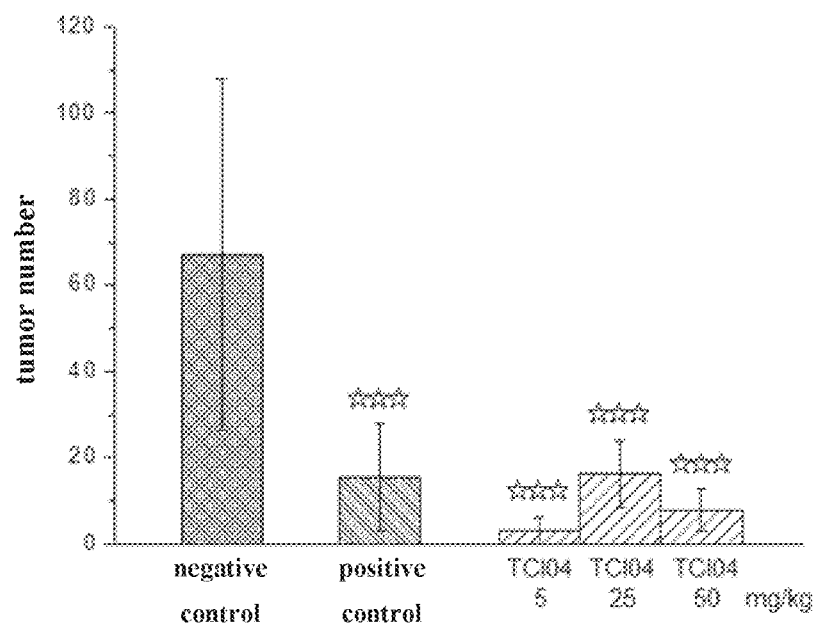
FIG. 16. The statistics of the metastatic tumors in lung in mice in Example 8.

1) Mice grouping, C57BL/6 of SPF grade, 5 weeks old, 18~22 g, 8 mice for each group. half male and half female;
2) The mother liquid of (S)2-(4'-methyl-3'-nitrobenzoylamino)-3-phenylpropionic acid for dosage form for oral administration was diluted with 1.5% CMC-Na solution to 5 mg/mL, 2.5 mg/mL, 0.5 mg/mL. The dosage for administration in mice was as follows, high dosage group of 50 mg/kg; Medium dosage group of 25 mg/kg; low dosage group of 5 mg/kg. The negative control was 1.5% CMC-Na solution; The positive control was 10 mg/mL of dosage form of 4-methyl-3-nitrobenzoic acid for oral administration, with dosage for administration of 100 mg/kg;
3) The tumors were carefully peeled off from κ-14 days mice bearing tumors of Lewis lung cancer in the sterilized condition, and the outside fat tissue was removed, and cut into small pieces. Then appropriate amount of physiological saline was added and homogenated in the glass homogenizer. After filtrating with 40 μM cell filter and counting cells, physiological saline was added to adjust the concentration to $5\times10^6$/mL. 0.2 mL cell suspension was inoculated at the right oxter for each mouse.
4) One week after inoculation of cell suspension, the administration was started, and the administration routine was intragastric infusion, with 0.2 mL once and twice a day for 21 days continuously;
5) After the completion of the experiment, the mice were sacrificed and the lungs were made into paraffin tissue sections, then stained by HE and the number of tumors were counted under microscope;
6) The experimental results were shown in FIGS. 15 and 16. For the negative control, there were many visible bulges on the surface of the lungs in mice and the shape of the lungs were abnormal; for the experimental group, few tumors with small volume were seen on the lungs and the shape of the lungs were substantially normal. According to the statistic analysis of the number of the tumors on the lungs, as compared with the negative control, 3 concentrations in the experimental group all had very significant difference (P<0.01); as compared with the positive control, 3 concentrations in the experimental group all had significant difference (P<0.05), which indicated that (S)2-(4'-methyl-3'-nitrobenzoylamino)-3-phenylpropionic acid effectively inhibited metastasis of Lewis lung cells in mice in vivo.

Example 9

The median lethal dose of (S)2-(4'-methyl-3'-nitrobenzoylamino)-3-phenylpropionic acid via intravenous administration was tested by mice acute toxicity assay.

1) Mice grouping, Kunming mice of clean grade, 10 weeks old, 30~40 g body weight, 10 mice for each group, half male and half female.
2) 10 groups in total, concentration distance between groups was 0.88. Sterilized water was added to the mother liquid II for dosage form administrated by intravenous injection to formulate into the required concentration and 0.2 ml was intravenously injected for each mouse, following 14 days observation. The dosage of administration for each group and the death numbers were recorded as follows:

|  | Dosage (mg/kg) | | | | | | | | | |
| --- | --- | --- | --- | --- | --- | --- | --- | --- | --- | --- |
|  | 500.0 | 440.0 | 387.2 | 340.7 | 299.8 | 263.8 | 232.1 | 204.2 | 179.7 | 158.1 |
| Death number | 10 | 10 | 10 | 9 | 7 | 3 | 2 | 2 | 0 | 0 |

Calculated according to Bliss algorithm, LD50=269.22 mg/kg, 95% confidence limits=249.2~290.78 mg/kg.

Example 10

The medium lethal dose of (S)2-(4'-methyl-3'-nitrobenzoylamino)-3-phenylpropionic acid via oral administration was tested by acute toxicity assay in mice.

1) Mice grouping: Kunming mice of clean grade, 10 weeks old, 30~40 g body weight, 5 mice for each group, and all of the mice were males or females.
2) 3.2 g (S)2-(4'-methyl-3'-nitrobenzoylamino)-3-phenylpropionic acid was added to 8 mL solution of 3% sodium carboxymethylcellulose solution, and the mixture was homogenated for 5 min at 30000 rpm with a homogenizer. Each mouse undergone administration of intragastric infusion with 0.5 ml at a dosage of 5000 mg/kg. The mice were observed for 14 days. If the death number was less than 2, the $LD_{50}$ was regarded as more than 5000 mg/kg; if the death number equals to or was more than 3, the main experiments will be performed. The experiment was repeated for 3 times and the result was recorded as follows:

| Death number | The first test | The second test | The third test |
| --- | --- | --- | --- |
| Male mice | 2 | 1 | 1 |
| Female mice | 2 | 2 | 1 |

From the three experimental results, the death numbers of male, female mice were both no more than 2, therefore, the $LD_{50}$ of (S) 2-(4'-methyl-3'-nitrobenzoylamino)-3-phenylpropionic acid via oral administration was more than 5000 mg/kg.

Example 11

The half inhibitory concentration of (S)2-(4'-methyl-3'-nitrobenzoylamino)-3-phenylpropionic acid for MDA-MB-231 cells was tested by MTT assay.

1) The MDA-MB-231 cells in logarithmic growth phase were seeded in the 96-well plate with a density of $4\times10^3$/0.2 ml. After culturing for 12 h, 20 ul drug was added, with the final concentration of 0, 50, 100, 200, 400, 600, 800, 1000, 1200, 1300, 1400, 1600, 1800, 2000, 2200, 2400, 2600, 2800, 3000 μM, followed by continuous culturing for 48 h.
2) 5 mg/mL MTT solution was prepared with sterilized PBS, filtered with 0.22 um film, and then diluted with medium to 1 mg/mL. The medium in the 96-well plate was discarded, and 100 μL 1 mg/mL MTT working solution was add, followed by continuous culturing for 5 h.

3) MTT working solution was discarded, and 150 μL DMSO was added to each well (note: to away from light), and then the plate was shaken on the horizontal shaker at 170 rpm for 10 min, followed by detecting the absorbance at 490 nm with microplate reader.

Figure 17:
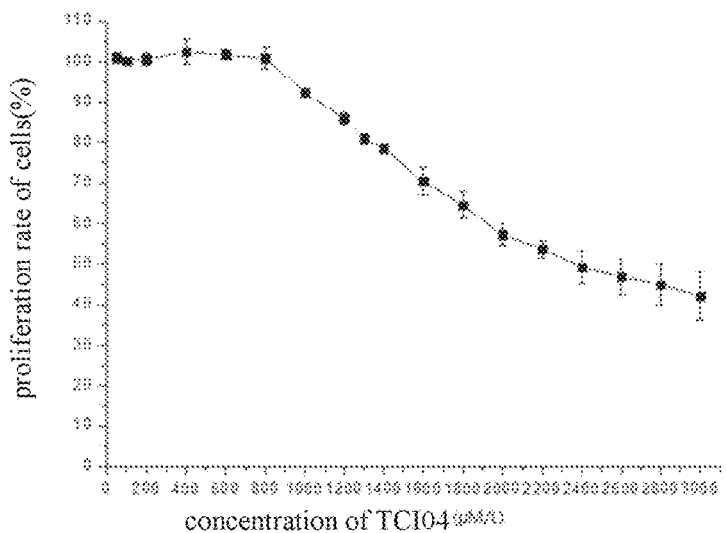
FIG. 17. The inhibition of (S)2-(4'-methyl-3'-nitrobenzoylamino)-3-phenylpropionic acid for the proliferation ability of MDA-MB-231 cells in Example 11.

4) The proliferation rates of MDA-MB-231 cells after treating with different concentrations of (S)2-(4'-methyl-3'-nitrobenzoylamino)-3-phenylpropionic acid were shown in FIG. 17. After calculation, $IC_{50}$=2449.07 μM.

Example 12

Synergistic effects of (S)2-(4'-methyl-3'-nitrobenzoylamino)-3-phenylpropionic acid and Paclitaxel was tested by MTT assay.

1) The MDA-MB-231 cells in logarithmic growth phase were seeded in the 96-well plate at a density of $4 \times 10^3$/0.2 ml. After culturing for 12 h, 10 μl Paclitaxel solution was added, with the final concentration of 0, 0.001, 0.01, 0.1, 1, 10, 50, 100, 200 μM, then 10 μL (S)2-(4'-methyl-3'-nitrobenzoylamino)-3-phenylpropionic acid PBS solution was add to half of the wells for each group with the final concentration of 20 μM, followed by continuous culturing for 24 or 48 h.

2) 5 mg/mL MTT solution was prepared with sterilized PBS, filtered with 0.22 μm film, and diluted with medium to 1 mg/mL. After discarding the medium in the 96-well plate, 100 μL 1 mg/mL MTT working solution was added, followed by continuous culturing for 5 h.

3) MTT working solution was discarded, and 150 μL DMSO was added per well (note: to away from light). The plate was shaken on a horizontal shaker at 170 rpm for 10 min, and then the absorbance at 490 nm was detected by microplate reader.

Figure 18:
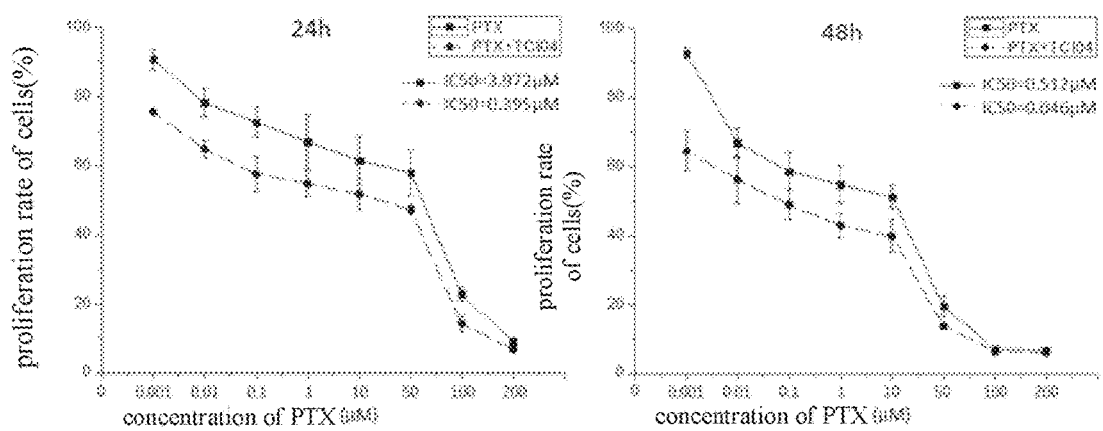
FIG. 18. The sensibilization of (S)2-(4'-methyl-3'-nitrobenzoylamino)-3-phenylpropionic acid on Paclitaxel in Example 12.

4) As shown in FIG. 18, after the addition of 20 μM (S)2-(4'-methyl-3'-nitrobenzoylamino)-3-phenylpropionic acid, the killing effect of Paclitaxel on cancer cells was significantly enhanced. After calculation, $IC_{50}$ after 24 h was decreased from 3.972 μM to 0.395 μM and $IC_{50}$ after 48 h was decreased from 0.512 μM to 0.046 μM. $IC_{50}$ after combination of the drugs was one tenth as compared with the original drug, which indicated that (S)2-(4'-methyl-3'-nitrobenzoylamino)-3-phenylpropionic acid and Paclitaxel had strong synergistic effect.

Example 13

The synthesis of 2-(4'-methyl-3'-nitrobenzoylamino)-3-indolyl propionic acid (TCI05), 2-(4'-methyl-3'-nitrobenzoylamino)-3-(4-hydroxy-phenyl)propionic acid (TCI06), 2-(4'-methyl-3'-nitrobenzenemethoxycarbonyl)-3-phenylpropionic acid (TCI07), 2-(4'-methyl-3'-nitrobenzenemethoxycarbonyl)-3-indolylpropionic acid (TCI08).

1) 0.01 mol tryptophan, tyrosine, 2-hydroxy-3-phenylpropionic acid, 2-hydroxy-3-indolyl propionic acid were weighed, 10 mL tetrahydrofuran was added and heated at 50☐ to dissolve. After resolution, 0.05 mol sodium carbonate was added, and stirred for 15 min, then catalytic amount of dimethylaminopyridine was added;

2) 0.03 mol 4-methyl-3-nitrobenzoic acid was weighed, and 90 mL dichlorosulfoxide was added and heated at 90 ☐ under reflux for 3 h. After evaporation and drying with a rotary evaporator, 2 mL tetrahydrofuran was added to dissolve the product, then the dissolved products was added dropwise to the solution described in step 1) with a constant pressure dropping funnel, followed by heating at 60 ☐ for 20 h to react;

3) After the completion of the reaction, the precipitate was removed by sucking filtration. The filtrate was dried by a rotary evaporator, and the precipitate was dissolved by adding 100 mL chloroform, followed by concentration by rotary evaporator.

4) The concentrate was separated by a silica gel chromatography column. First, ethyl acetate:petroleum ether=1:2 (1.4% glacial acetic acid) was used to elute 4-methyl-3-nitrobenzoic acid, then methanol:dichloromethane=1:1, with 1.4% glacial acetic acid was used to elute the target product;

5) The mobile phase contain the target product was combined, and spun to be substantially dry with a rotary evaporator, then put into vacuum drying oven and dried at 45 ☐ for 72 h;

6) The yield was 70-80%.

Example 14

The inhibiting ability of 2-(4'-methyl-3'-nitrobenzoylamino)-3-indolylpropionic acid (TCI05), 2-(4'-methyl-3'-nitrobenzoylamino)-3-(4-hydroxy-phenyl) propionic acid (TCI06), 2-(4'-methyl-3'-nitrobenzenemethoxycarbonyl)-3-phenylpropionic acid (TCI07), 2-(4'-methyl-3'-nitrobenzenemethoxycarbonyl)-3-indolylpropionic acid (TCI08) for the migration of human breast cancer cells MDA-MB-231 was tested by scratching assay.

Figure 19:
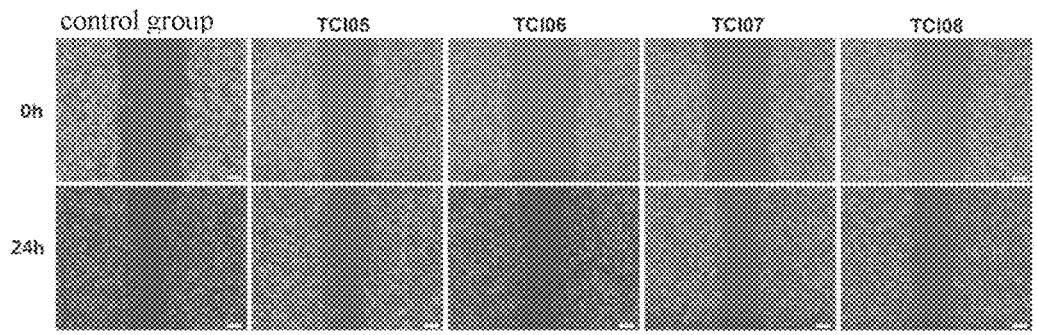
FIG. 19. The inhibition of TCI05, TCI06, TCI07, TCI08 for the migration ability of MDA-MB-231 cells in Example 14.
Figure 20:
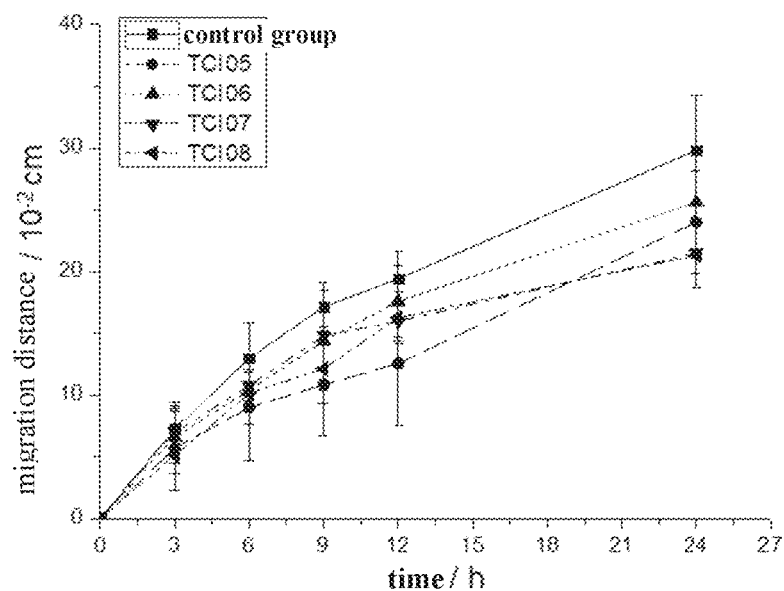
FIG. 20. The statistics of the inhibition of TCI05, TCI06, TCI07, TCI08 for the migration of MDA-MB-231 cells in Example 14.
Figure 21:
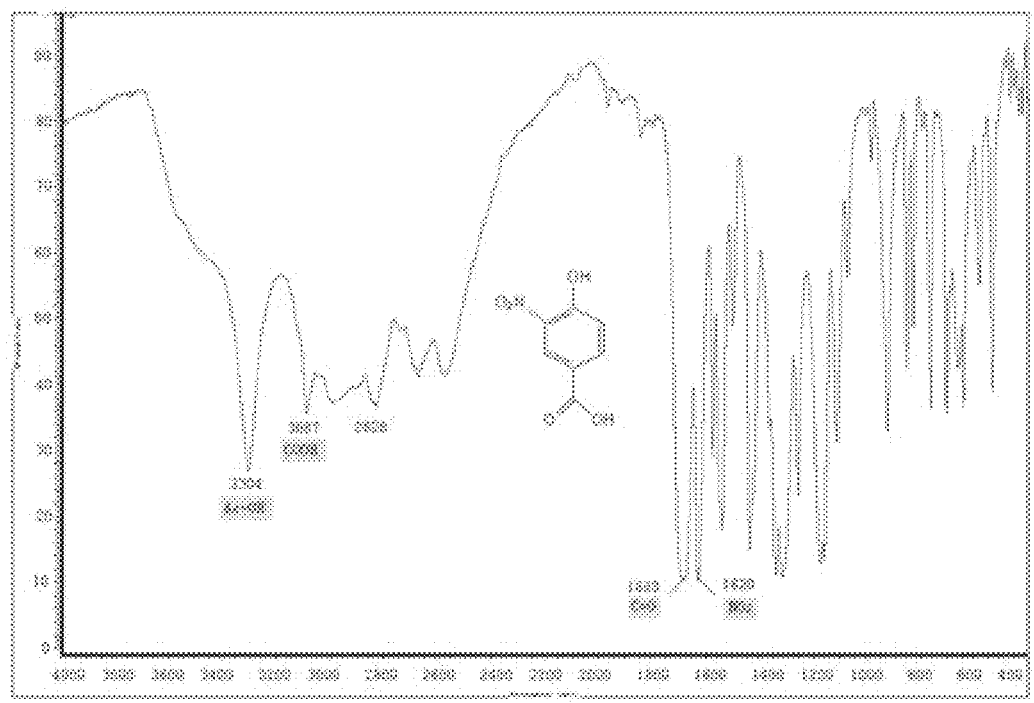
FIG. 21. The infrared spectrum of 4-hydroxy-3-nitrobenzoic acid in Example 15.
Figure 22:
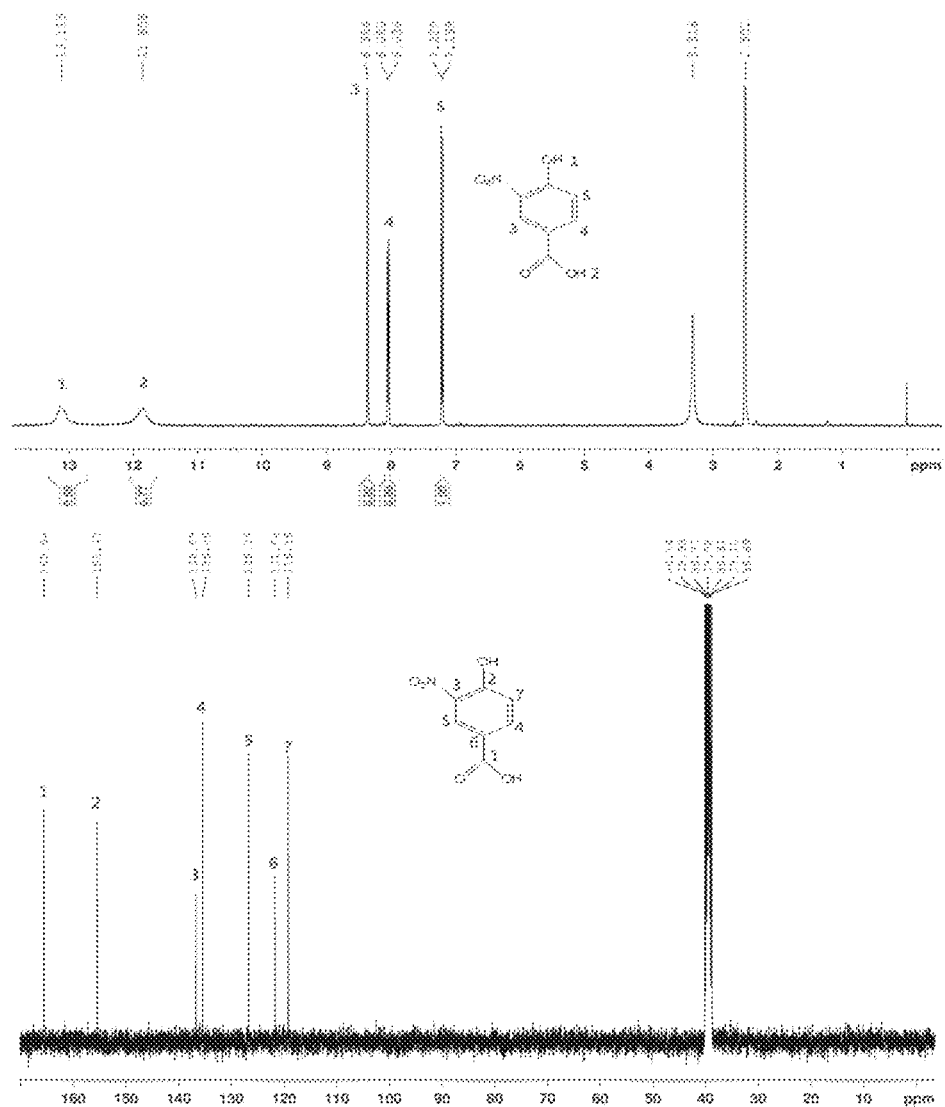
FIG. 22. The NMR spectrum of 4-hydroxy-3-nitrobenzoic acid in Example 15.
Figure 23:
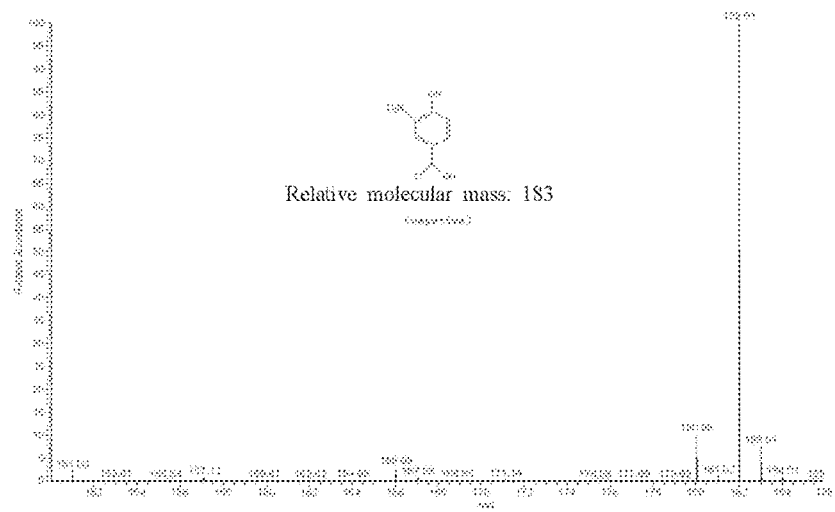
FIG. 23. The mass spectrum of 4-hydroxy-3-nitrobenzoic acid in Example 15.
Figure 24:
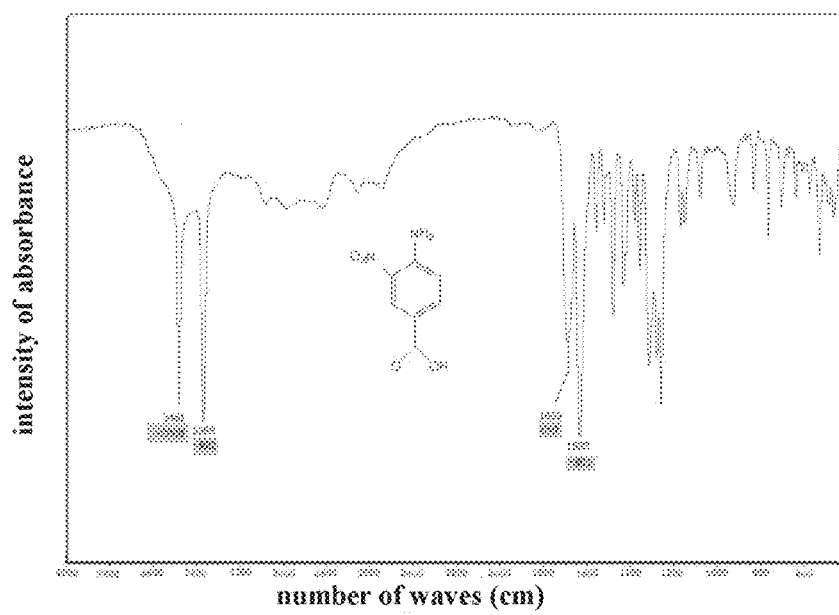
FIG. 24. The infrared spectrum of 4-amino-3-nitrobenzoic acid in Example 15.
Figure 25:
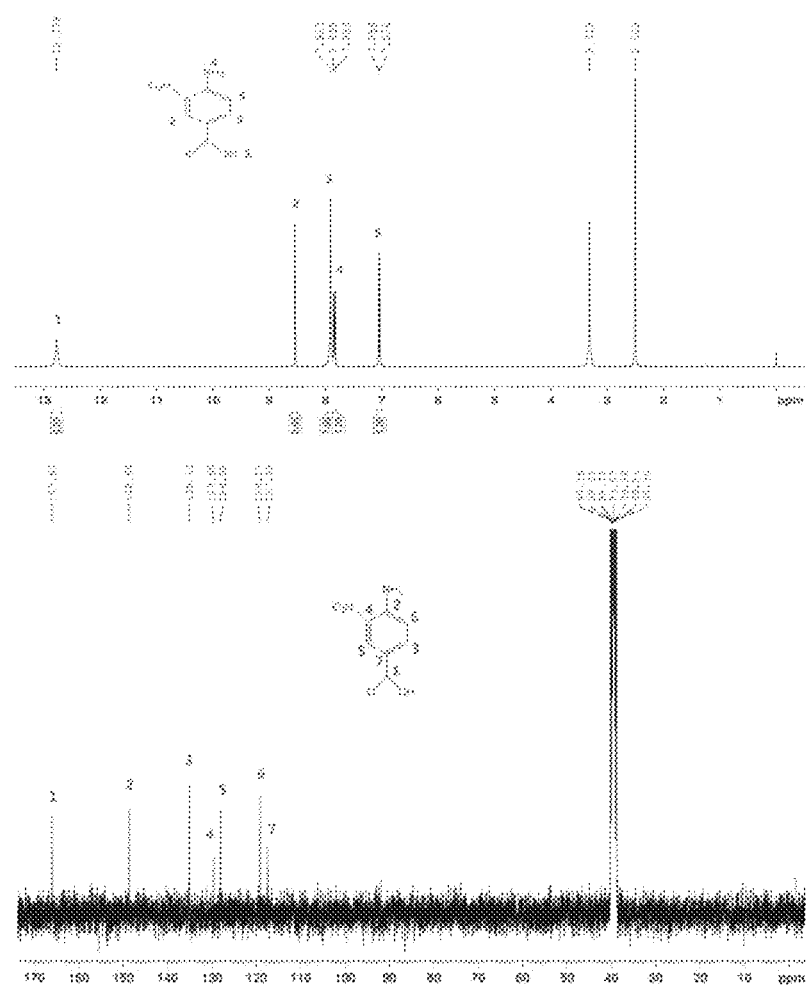
FIG. 25. The NMR spectrum of 4-amino-3-nitrobenzoic acid in Example 15.
Figure 26:
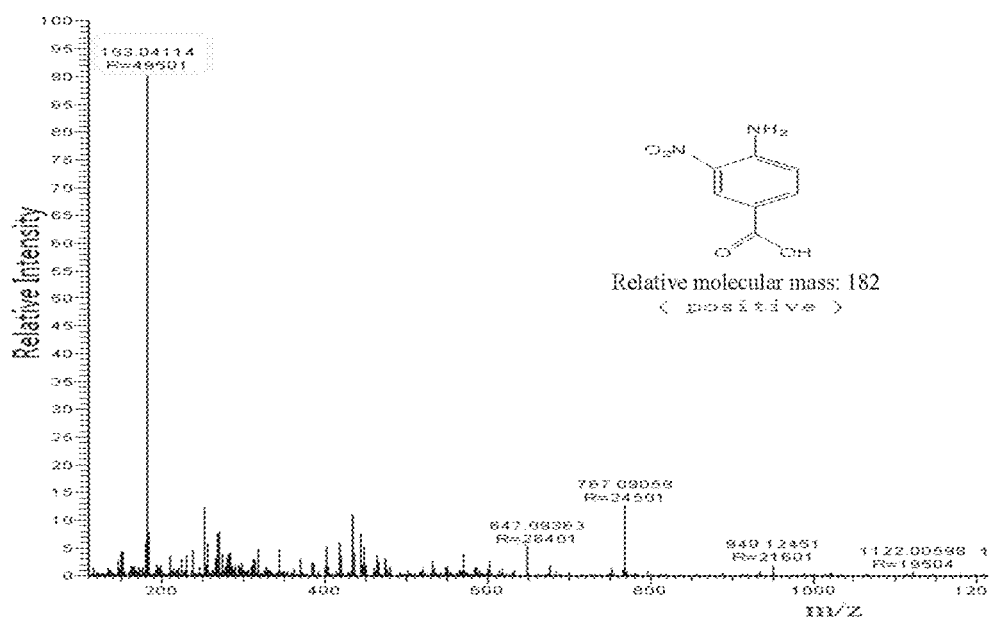
FIG. 26. The mass spectrum of 4-amino-3-nitrobenzoic acid in Example 15.

The MDA-MB-231 cells in logarithmic growth phase were seeded in the 6-well plate at a density of $1 \times 10^6$/3 ml, and 12 h later, TCI05, TCI06, TCI07, TCI08 (formulation was the same as TCI04) was added, 150 μl per well, with the final concentration of 20 μmol/L. The negative control was 150 μL sterilized water with 2% DMSO. 48 h later, 200 ul tips were used to scratch, and after washing 4 times with PBS, 3 ml medium without fetal bovine serum was added per well. Under the inverted microscope, the distance of cell migration was recorded every 3 h, and photos were taken at 0 h and 24 h. Experimental result: the coalescence speed of cell scratch in experimental group was apparently slower than the negative control, indicating that TCI05, TCI06, TCI07, TCI08 obviously inhibit the migration ability of MDA-MB-231 cells. The experimental results were shown in FIGS. 19 and 20.

Example 15

The characterization of the spectrum of 4-hydroxy-3-nitrobenzoic acid and 4-amino-3nitrobenzoic acid 4-hydroxy-3-nitrobenzoic acid and 4-amino-3nitrobenzoic acid were purchased from Beijing J&K Scientific Co. Ltd, and the structures of them were identified by infrared spectrum, NMR, mass spectra (See FIGS. 21-26).

Example 16

The inhibiting ability of 4-hydroxy-3-nitrobenzoic acid and 4-amino-3nitrobenzoic acid for the migration of human breast cancer cell MDA-MB-231 was tested by scratching assay.

Three lines were marked on the underside of 6-well plate, MDA-MB-231 breast cancer cells in logarithmic growth phase were digested with 0.7 mL 0.08% trypsin for 1 min, and the digestion was stopped with complete culture medium. After centrifugation at 1000 r/min for 3 min, the supernatant was discarded, then 3 mL complete culture medium was added. After pipetting to make suspension of single cell, the cells in the cell suspension was counted, and the concentration of the cells was adjusted to a density of $5\times10^5$ cells/well to plate the 6 wells plate, and 6 groups of drugs containing complete culture medium (DMEM+10% FBS+1% Penicillin-Streptomycin+drug) were added. After culturing in a incubator for 12 h until the cells were attached, the culture medium was removed, 20 μL tips were used to scratch vertically to the three transverse lines on the underside to obtain 6 distances for counting, and after washing with phosphate buffered saline (PBS) three times, 6 groups of drugs containing culture medium without FBS (DMEM+drug) were added respectively, and the width of the scratches were observed and recorded at 0 h, 3 h, 6 h, 9 h, 12 h and 24 h under inverted microscope, with 6 distances being recorded per well, wherein, photos were taken with inverted microscope at 0 h and 24 h for recording.

Figure 27:
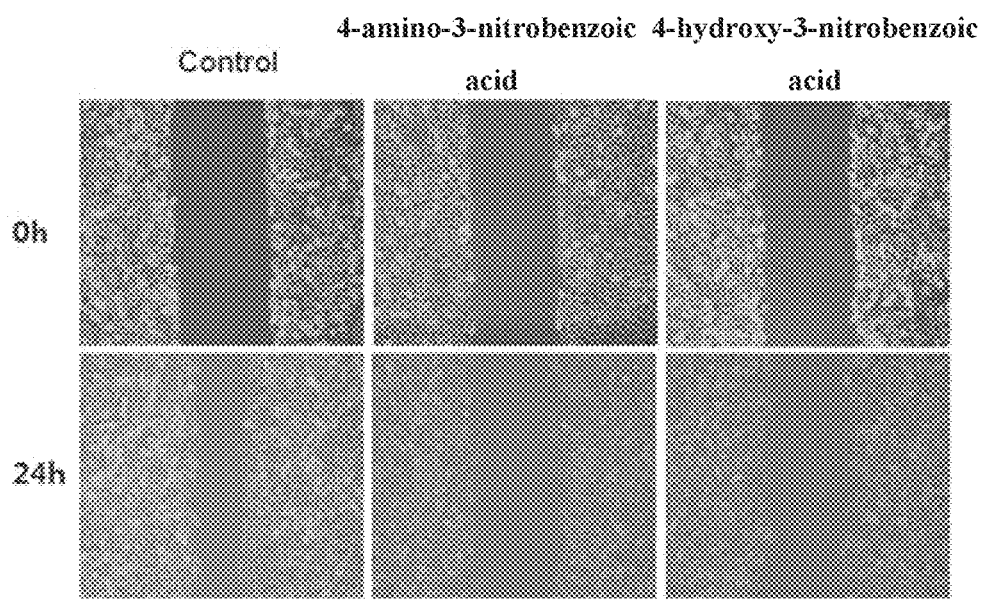
FIG. 27. The inhibition of 4-hydroxy-3-nitrobenzoic acid and 4-amino-3-nitrobenzoic acid for the migration of human breast cancer cell MDA-MB-231 in Example 16.

For the experimental results, see the following Table and FIG. 27, the coalescence speed of cell scratch in experimental group was apparently slower than the negative control, indicating that 4-hydroxy-3-nitrobenzoic acid and 4-amino-3nitrobenzoic acid obviously inhibit the migration ability of MDA-MB-231 cell.

|  | control | 4-amino-3-nitrobenzoic acid | 4-hydroxy-3-nitrobenzoic acid |
|---|---|---|---|
| average $10^{-2}$ mm | 13.1667 | 8.1667 | 8 |
| variance | 1.1690 | 1.4720 | 0.8944 |
| P value |  | 0.004 | 0.049 |

The invention claimed is:

1. A method for treating cancer in a subject, comprising administering a compound to the subject, wherein the compound is represented by formula I:

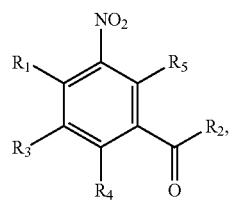

where $R_1$ is selected from the group consisting of C1-C6 hydrocarbon group, —NH$_2$, —OH, —O(CH$_2$)$_n$CH$_3$ (n=0, 1 or 2), —N(CH$_3$)$_2$, —CH$_2$N(CH$_3$)$_2$;

$R_2$ is α-amino acid

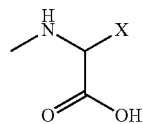

or α-hydroxy acid

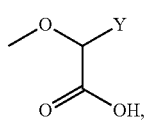

where X, Y are

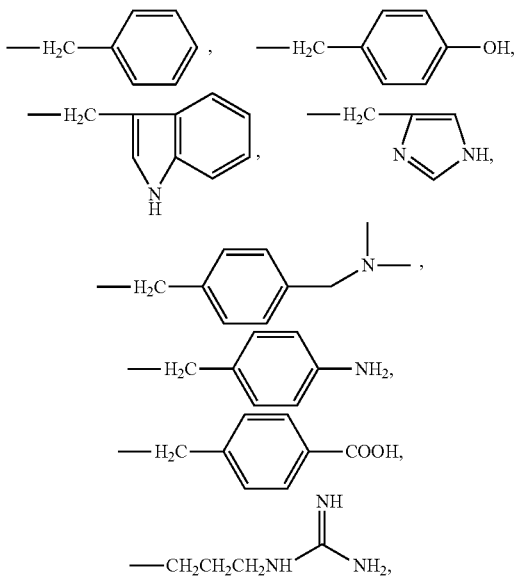

—CH$_3$, —CH$_2$OH, —CH(OH)CH$_3$, —CH$_2$SH, —CH$_2$CH$_2$SCH$_3$, —CH$_2$CONH$_2$, —CH$_2$CH$_2$COOH, —CH$_2$CH$_2$CH$_2$CH$_2$NH$_2$, or —CH$_2$CH$_2$CONH$_2$; and $R_3$ to $R_5$ are H or C1-C6 hydrocarbon group.

2. A method for inhibiting tumor metastasis in a subject, comprising administering a compound to the subject, wherein the compound is represented by formula I:

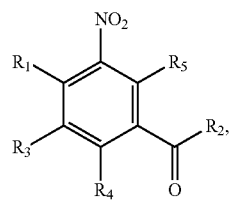

where $R_1$ is selected from the group consisting of C1-C6 hydrocarbon group, —NH$_2$, —OH, —O(CH$_2$)$_n$CH$_3$ (n=0, 1 or 2), —N(CH$_3$)$_2$, —CH$_2$N(CH$_3$)$_2$;

$R_2$ is α-amino acid

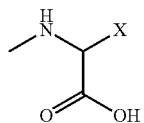

or α-hydroxyl acid

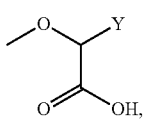

where X, Y are

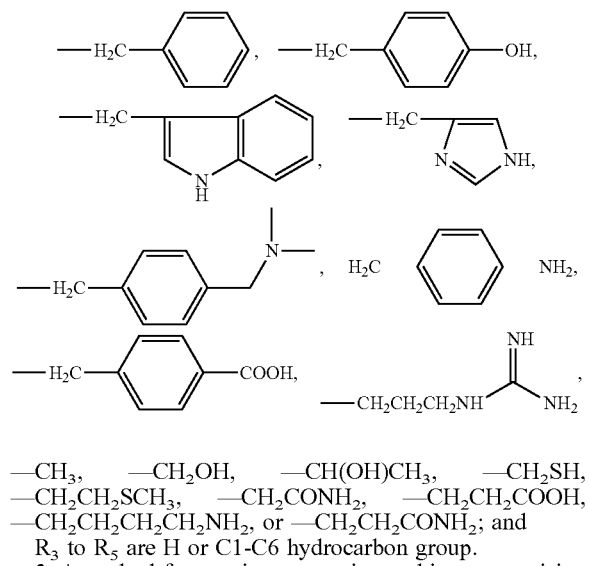

—CH₃, —CH₂OH, —CH(OH)CH₃, —CH₂SH, —CH₂CH₂SCH₃, —CH₂CONH₂, —CH₂CH₂COOH, —CH₂CH₂CH₂CH₂NH₂, or —CH₂CH₂CONH₂; and
R₃ to R₅ are H or C1-C6 hydrocarbon group.

3. A method for treating cancer in a subject, comprising administering a compound and another anti-tumor drug to the subject,
wherein the another anti-tumor drug includes a cytotoxic anti-tumor drug, and
wherein the compound is represented by formula I:

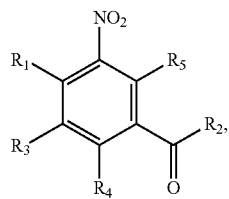

where R₁ is selected from the group consisting of C1-C6 hydrocarbon group, —NH₂, —OH, —O(CH₂)ₙCH₃ (n=0, 1 or 2), —N(CH₃)₂, —CH₂N(CH₃)₂;
R₂ is α-amino acid

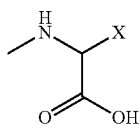

or α-hydroxyl acid

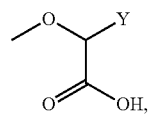

where X, Y are

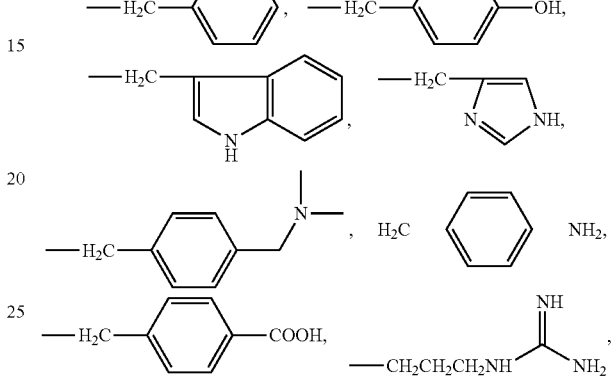

—CH₃, —CH₂OH, —CH(OH)CH₃, —CH₂SH, —CH₂CH₂SCH₃, —CH₂CONH₂, —CH₂CH₂COOH, —CH₂CH₂CH₂CH₂NH₂, or —CH₂CH₂CONH₂; and
R₃ to R₅ are H or C1-C6 hydrocarbon group.

4. The method according to claim 3, wherein the another anti-tumor drug is Paclitaxel.

5. The method of claim 1, wherein R₁ is C1-C6 hydrocarbon group, R₂ is α-amino acid, and R₃ to R₅ is H.

6. The method of claim 1, wherein the compound is (S)2-(4'-methyl-3'-nitrobenzoylamino)-3-phenyl propionic acid.

7. The method of claim 2, wherein R₁ is C1-C6 hydrocarbon group, R₂ is α-amino acid, and R₃ to R₅ is H.

8. The method of claim 2, wherein the compound is (S)2-(4'-methyl-3'-nitrobenzoylamino)-3-phenyl propionic acid.

9. The method of claim 3, wherein R₁ is C1-C6 hydrocarbon group, R₂ is α-amino acid, and R₃ to R₅ is H.

10. The method of claim 3, wherein the compound is (S)2-(4'-methyl-3'-nitrobenzoylamino)-3-phenyl propionic acid.

* * * * *